US010617357B2

(12) United States Patent
Miller et al.

(10) Patent No.: US 10,617,357 B2
(45) Date of Patent: Apr. 14, 2020

(54) SWAPPABLE WEARABLE DEVICE

(71) Applicant: Halo Wearables, LLC, Plymouth, MI (US)

(72) Inventors: Devin Warner Miller, Morgan, UT (US); David Rich Miller, Morgan, UT (US); Jeffrey Michael Lee, Morgan, UT (US)

(73) Assignee: Halo Wearables, LLC, Morgan, UT (US)

( * ) Notice: Subject to any disclaimer, the term of this patent is extended or adjusted under 35 U.S.C. 154(b) by 1395 days.

(21) Appl. No.: 14/467,021

(22) Filed: Aug. 24, 2014

(65) Prior Publication Data

US 2016/0051191 A1 Feb. 25, 2016

(51) Int. Cl.
| A61B 5/00 | (2006.01) |
| A61B 5/0205 | (2006.01) |
| G16H 20/30 | (2018.01) |
| G16H 50/30 | (2018.01) |
| G16H 40/67 | (2018.01) |

(52) U.S. Cl.
CPC .............. *A61B 5/681* (2013.01); *A61B 5/002* (2013.01); *A61B 5/0205* (2013.01); *G16H 20/30* (2018.01); *G16H 40/67* (2018.01); *G16H 50/30* (2018.01); *A61B 2560/0456* (2013.01); *A61B 2562/08* (2013.01)

(58) Field of Classification Search
CPC ...... A61B 5/002; A61B 5/681; G06F 19/3418
See application file for complete search history.

(56) References Cited

U.S. PATENT DOCUMENTS

| 8,738,925 B1* | 5/2014 | Park | H04B 7/26 713/186 |
| 8,784,274 B1* | 7/2014 | Chuang | G09B 19/0038 482/9 |
| 8,947,226 B2* | 2/2015 | Dugan | A61B 5/02 340/539.1 |
| 2008/0201169 A1* | 8/2008 | Galasso | G06F 19/3418 705/2 |
| 2009/0082692 A1* | 3/2009 | Hale | A61B 5/0476 600/544 |
| 2009/0088605 A1* | 4/2009 | Ross | A61B 5/0002 600/300 |
| 2010/0067723 A1* | 3/2010 | Bergmann | H04M 1/6066 381/315 |
| 2010/0145236 A1* | 6/2010 | Greenberg | A61B 5/1101 600/595 |
| 2011/0224564 A1* | 9/2011 | Moon | A61B 5/00 600/509 |

(Continued)

Primary Examiner — John R Downey
(74) Attorney, Agent, or Firm — Miller IP Law, LLC

(57) ABSTRACT

A technology for a swappable wearable device that is operable to monitor one or more physiological parameters of a user. Physiological measurement data from a physiological measurement sensor attached to the swappable wearable device or a physiological measurement sensor in communication with the swappable wearable device can be received at the swappable wearable device. The physiological measurement data can be stored on a non-transitory computer readable medium coupled to swappable wearable device. The stored physiological measurement data can be communicated to another swappable wearable device or a synchronization platform when a selected event occurs.

21 Claims, 32 Drawing Sheets

(56) References Cited

U.S. PATENT DOCUMENTS

| | | | |
|---|---|---|---|
| 2012/0290266 A1* | 11/2012 | Jain | G16H 40/63 |
| | | | 702/187 |
| 2014/0156228 A1* | 6/2014 | Molettiere | G16H 10/60 |
| | | | 702/189 |
| 2014/0163927 A1* | 6/2014 | Molettiere | A61B 5/0002 |
| | | | 702/189 |
| 2014/0241540 A1* | 8/2014 | Hodges | H04M 1/6066 |
| | | | 381/74 |
| 2014/0246924 A1* | 9/2014 | Proud | H04B 5/0037 |
| | | | 307/114 |
| 2015/0006870 A1* | 1/2015 | Switzer | G06F 9/4401 |
| | | | 713/1 |
| 2015/0286813 A1* | 10/2015 | Jakobsson | G06F 21/35 |
| | | | 726/9 |
| 2016/0081625 A1* | 3/2016 | Kim | H04W 4/70 |
| | | | 600/301 |

* cited by examiner

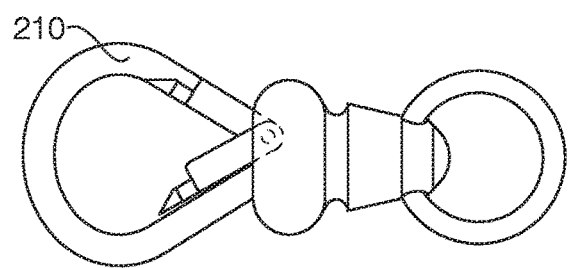
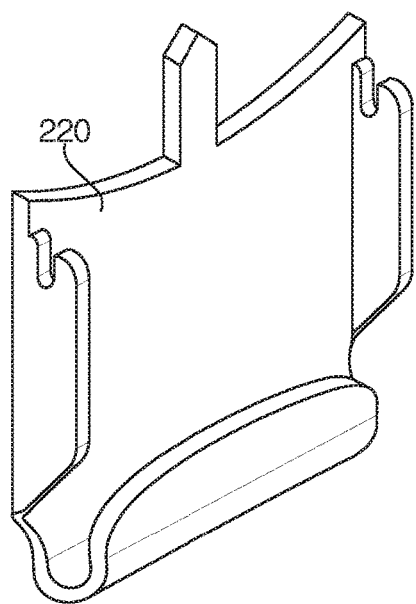
FIG. 2a                    FIG. 2b
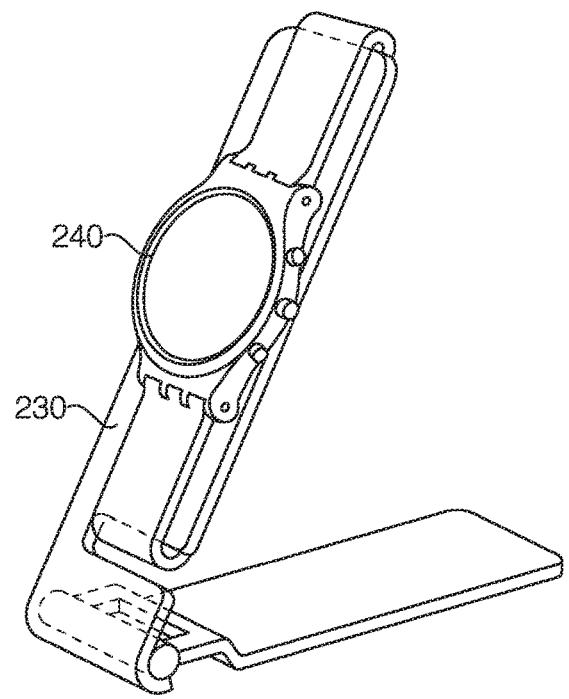
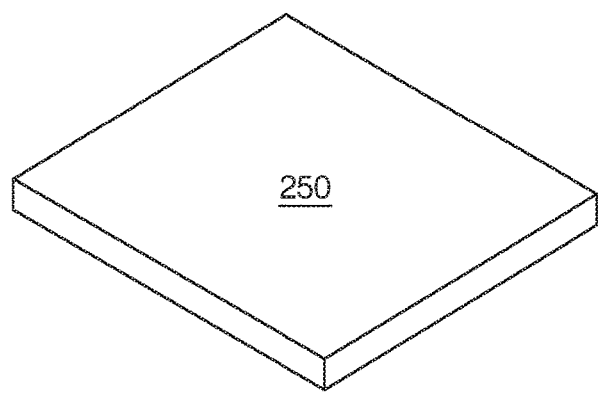
FIG. 2c                    FIG. 2d

SWAPPABLE WEARABLE DEVICE

BACKGROUND

Medical professionals often use medical monitoring equipment in diagnosing or treating a medical patient. A patient can come into a medical facility where a medical professional can use the medical monitoring equipment to take a single measurement, such as a blood draw, or a take a measurement for a short duration. Wearable devices such as a finger pulse oximeter enable a patient to take spot-checking medical measurements on a periodic basis, but still do not enable a patient to take measurements on a continuous basis. Recently, wearable device have continued to develop to enable individuals to take measurements for longer durations. However, wearable devices have to be removed for certain events. In one example, a wearable device powered by a battery can require removing the wearable device from the individual to recharge the wearable device. In another example, an individual may need to remove the wearable device to perform software, firmware, and/or hardware updates or repairs. During the period where the wearable device is removed from the individual for the selected event, there is a substantial gap in measurement data that prohibits continuous or near-continuous measurement taking.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein:

FIG. 2a shows a synchronization platform configured as a hook in accordance with an example;

FIG. 2b shows a synchronization platform configured as a hanger in accordance with an example;

FIG. 2c shows a synchronization platform configured as a holder with a swappable wearable device coupled or attached to the holder in accordance with an example;

FIG. 2d shows a synchronization platform configured as a plate in accordance with an example;

Reference will now be made to the exemplary embodiments illustrated, and specific language will be used herein to describe the same. It will nevertheless be understood that no limitation of the scope of the invention is thereby intended.

DETAILED DESCRIPTION

Data collected from continuous or near continuous monitoring can provide unbiased or less biased measurement data. The physiology of an individual is constantly changing. For example, over the space of a few hours a hydration level of an individual may increase or decrease by a large margin based on the amount of fluid the individual intakes or excretes. In another example, a heart rate of an individual can increase or decrease by a large margin based on an exertion or activity level of the individual, such as working out or sleeping. In another example, a medical condition of an individual may deteriorate quickly over a short period of time, such as a few minutes or a few hours and require continuous or near-continuous monitoring.

For an individual monitoring a medical condition using a wearable device, continuous monitoring of the medical condition using a wearable device can enable the individual to monitor trends in measurement data, receive constant monitoring to detect early signs of a medical event, and/or monitor the effectiveness of a pharmaceutical drug. Traditional wearable devices require that the individual remove the wearable device for a period of time for selected events, such as recharging a battery of the wearable device or performing updates or repairs to the wearable device. For example, an individual may remove a wearable device before going to bed, plug the device in a power adapter to recharge the wearable device, and the replace the wearable device in the morning after the wearable device has fully recharged. During the period of time that the individual has removed the wearable device for recharging, the wearable device does not take measurements of the individual. The period of time when the wearable device is not taking measurements can cause gaps in measurement data, bias the measurement data, disrupt data trending analysis, and so forth. In one embodiment, a gap in measurement data can miss capturing critical event data, such as events associated with sleeping (e.g. sleep apnea, hypoglycemia, and so forth) or waking events (such as a myocardial infarction).

Figure 1:
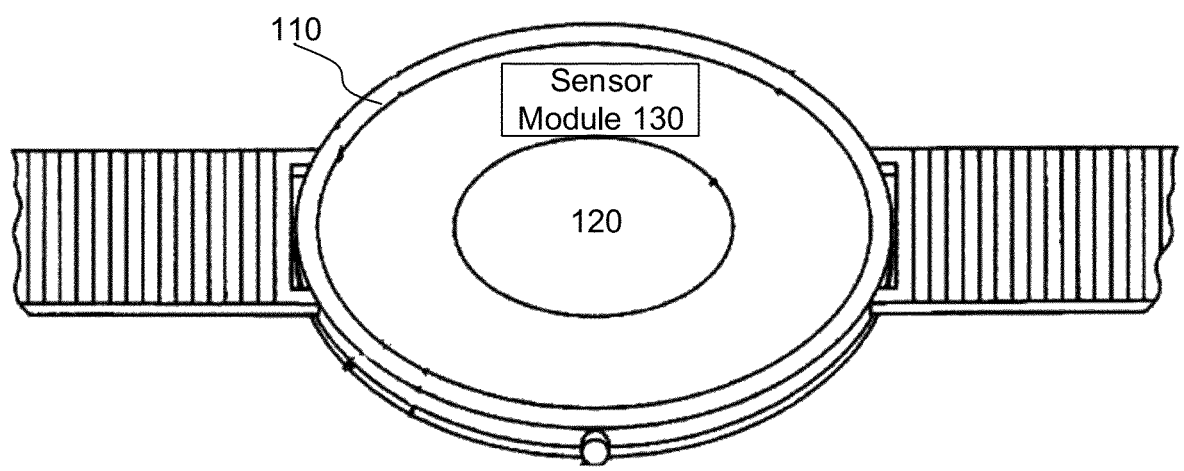
FIG. 1 shows bottom view of a swappable wearable device that can be used to take selected measurements using one or more sensors in accordance with an example.

In one example, an individual can wear a swappable wearable device to take a selected measurement and/or monitor measurement data. FIG. 1 shows bottom view of a swappable wearable device 110, such as a swappable wearable wristband, that can be used to take selected measurements using one or more sensors 120. In one embodiment, the one or more sensors 120 can be a bio-impedance sensor, an accelerometer, a three dimensional (3D) accelerometer, a gyroscope, a light sensor, an optical sensor, a spectroscopy sensor, a heart rate monitor, a blood pressure sensor, a pulse oximeter, and so forth. In one example, the swappable wearable device 110 can include a sensor module 130 to receive measurement information from the one or more sensors 120 and analyze the measurement information to determine selected physiological information and/or medical information, such as a hydration level of the user, cardiac information of the user (such as blood pressure or heart rate), an blood oxygen level of the user, and so forth.

In one embodiment, when a removal event of a first swappable wearable device is pending or approaching, such as when a battery level of the first swappable wearable device decreases below a selected level or the first swappable wearable device may be removed from the individual for repairs, bathing, and so forth, the first swappable wearable device can synchronize selected sync data of the first swappable wearable device with a second swappable wearable device. In one embodiment, the selected sync data can include user preference information, measurement data, calibration information, medical record information, medical patient information, medical measurement information, identification information, and so forth. In one embodiment, synchronizing selected sync data can be used to normalizing the measurements or data of a first device, such as a swappable wearable device, to measurements or data of a second device, such as another swappable wearable device. The first swappable wearable device can be replaced with the second swappable wearable device and the second swappable wearable device can continue to take measurements from the time that the first swappable wearable device stopped taking measurements using the selected sync data. One advantage of replacing the first swappable wearable device with the second swappable wearable device at a removal event is to provide continuous or near-continuous measurement data.

In one embodiment, a swappable wearable device can enable a continuous or near-continuous monitoring of one or more measurements of an individual. In another embodiment, near-continuous measurement data can be measurement data with a minor or slight gap in the measurement data during a time period when the first swappable wearable device is removed and replaced with the second swappable wearable device. In one example, an individual can temporarily wear the first swappable wearable device and the second swappable wearable device at the same time. In this example, the first swappable wearable device and the second swappable wearable device can synchronize measurement taking and/or measurement data before the first swappable wearable device is removed to provide for continuous measurement taking, e.g. measurement data without a gap during the replacement period of the first swappable wearable device. In another embodiment, the first swappable wearable device and the second swappable wearable device can follow a handover procedure to provide for continuous or near-continuous measurement taking during the removal event.

In one configuration, a swappable wearable device can synchronize the selected sync data with another swappable wearable device. In another configuration, the swappable wearable device can synchronize the selected sync data with a synchronization platform device. In one embodiment, the synchronization platform can be a platform such as a disk, a plate, a block, a hook, a cylinder, or other platform configurations. FIGS. 2a-2d show various exemplary embodiments of a synchronization platform. FIG. 2a shows a synchronization platform configured as a hook 210. In one example, a swappable wearable device can be hung from the hook. FIG. 2b shows a synchronization platform configured as a hanger 220. In one example, a swappable wearable device can be hung from the hanger. FIG. 2c shows a synchronization platform configured as a holder 230 with a swappable wearable device 240 coupled or attached to the holder 230. FIG. 2d shows a synchronization platform configured as a plate 250.

Figure 3:
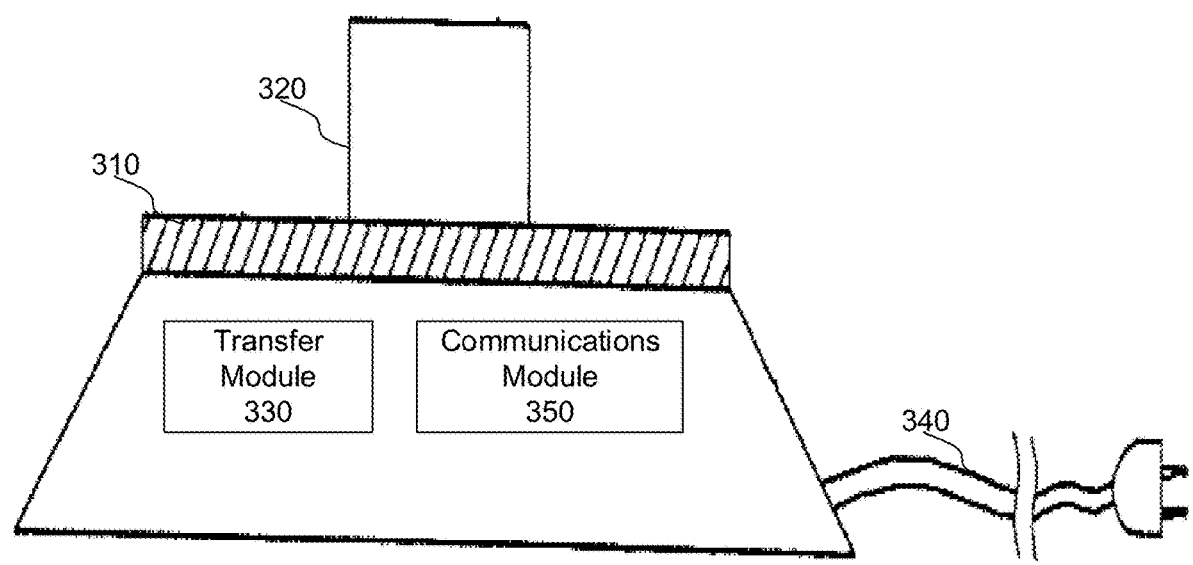
FIG. 3 shows an exemplary embodiment of a synchronization platform configured to transfer data and/or power with a swappable wearable device in accordance with an example.

FIG. 3 shows another exemplary embodiment of a synchronization platform 310 configured to transfer data and/or power with a swappable wearable device 320. In one embodiment, the synchronization platform can be configured to communicate data, such as sync data, with the swappable wearable device using a transfer module 330. In another embodiment, the synchronization platform 310 can be configured to transfer power with the swappable wearable device 320 using the transfer module 330. In one example, the synchronization platform 310 can transfer power using a physical electrical connection, such as a universal serial bus (USB) connection. In another example, the transfer module 330 and/or the synchronization platform 310 can include one or more wireless transfer coils and the synchronization platform 310 can be configured to wirelessly transfer power to the swappable wearable device 320 using the one or more wireless transfer coils.

In one configuration, the synchronization platform 310 can be connected to a power outlet (such as a wall power outlet) and/or a communication port (such as an Ethernet port) using a transfer connector 340. In one embodiment, the synchronization platform 310 can receive power from the power outlet using the transfer connector 340. In another embodiment, the synchronization platform 310 can communicate data, such as sync data, with another synchronization platform or another computing device (such as a server or cloud storage device as discussed in the proceeding paragraphs) using the transfer connector 340. In another embodiment, the synchronization platform 310 can communicate data with one or more swappable wearable devices, one or more synchronization platforms, and/or other devices using a communication module 350. In one embodiment, the communications module 350 can communicate the data using a cellular network and/or a wireless network.

In one example, the communications network can be a cellular network that may be a third generation partnership project (3GPP) release 8, 9, 10, 11, or 12 or Institute of Electronics and Electrical Engineers (IEEE) 802.16p, 802.16n, 802.16m-2011, 802.16h-2010, 802.16j-2009, 802.16-2009. In another embodiment, communications network can be a wireless network (such as a wireless fidelity (Wi-Fi) network) that may follow a standard such as the IEEE 802.11-2012, IEEE 802.11ac, or IEEE 802.11ad standard. In another embodiment, the communications network can be a Bluetooth connection such as Bluetooth v1.0, Bluetooth v2.0, Bluetooth v3.0, or Bluetooth v4.0. In another embodiment, the communications network can be a Zigbee connection such as IEEE 802.15.4-2003 (Zigbee 2003), IEEE 802.15.4-2006 (Zigbee 2006), IEEE 802.15.4-2007 (Zigbee Pro). In one embodiment, the synchronization platform and the swappable wearable device can use near field communication, or induction communication to communicate information between the synchronization platform and the swappable wearable device.

In one embodiment, the swappable wearable device can communicate measurement information to the synchronization platform at selected times of the day. In one example, the swappable wearable device can communicate sync data with the synchronization platform at a selected time when the user wakes up in the morning and at a selected time when the user goes to sleep at night. In another embodiment, the synchronization platform can communicate sync data with other devices such as computers, phones, tablets, medical equipment, display devices, and so forth.

Figure 4:
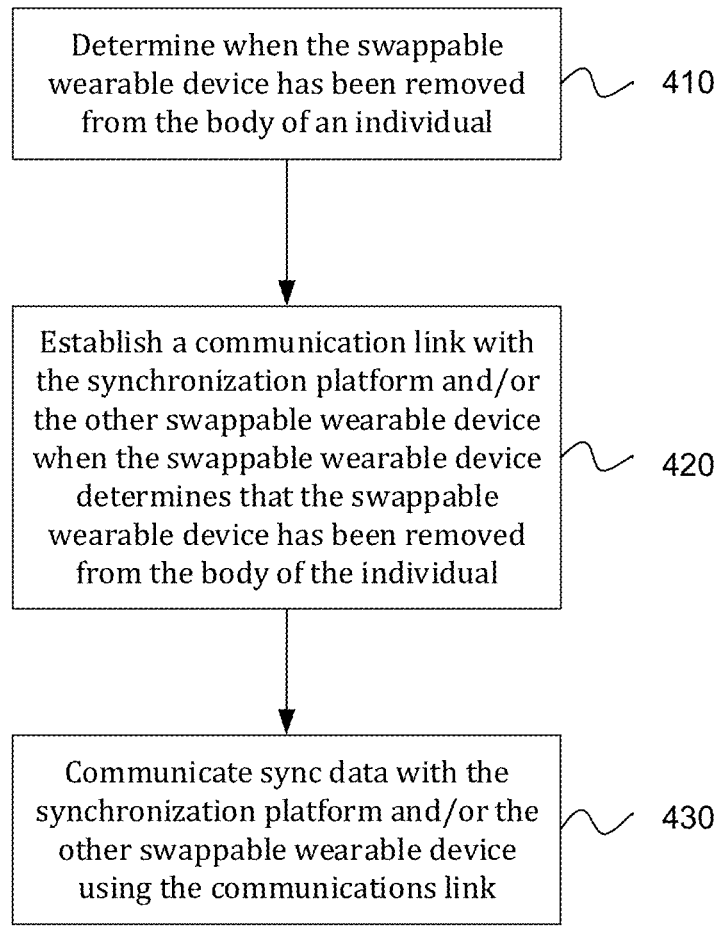
FIG. 4 depicts the functionality of circuitry of a swappable wearable device operable to transfer data with a synchronization platform in accordance with an example.

FIG. 4 shows a flow chart 400 illustrating a functionality of one embodiment of circuitry with a swappable wearable device operable to transfer data with a synchronization platform. The functionality may be implemented as a method or the functionality may be executed as instructions on a machine, where the instructions are included on at least one computer readable medium or one non-transitory machine readable storage medium. The circuitry can be configured to determine when the swappable wearable device has been removed from the body of an individual, as in block 410. In one embodiment, the circuitry can monitor one or more sensors of the swappable wearable device to determine when the sensors are no longer taking measurements of the user of the swappable wearable device. In another embodiment, the one or more sensors can include: an optical sensor, an impedance sensor, a bio-impedance sensor, an electrocardiogram (ECG) sensor, an accelerometer, an altimeter, a pulse oximeter, a fluid level sensor, an oxygen saturation sensor, a body temperature sensor, a plethysmograph sensor, a respiration sensor, a breath sensor, a cardiac sensor, a hydration level sensor, a humidity sensor, ambient temperature sensor, altitude sensor, barometer, a gyroscope sensor, a vibration sensor, an accelerometer sensor, 3d accelerometer sensor, force sensor, pedometer, strain gauge, and so forth. In one example, the sensors may no longer be taking measurements of the user when there is a sudden shift or change in measurement data of one or more sensors of the swappable wearable device. In another example, the sensors may no longer taking measurements of the user when one or more measurements is zero, near zero, or unknown. In another example, the sensors are no longer taking measurements of the user when one or more measurements are outside a selected threshold measurement range. When the sensors are no longer taking measurements of the user of the swappable wearable device, the swappable wearable device can determine that the swappable wearable device has been removed from the user and can communicate sync data with to the synchronization platform or another swappable wearable device.

The swappable wearable device can be further configured to establish a communication link, such as a cellular network communications link, a wireless network communications link, a device to device (D2D) communications link, a peer-to-peer (P2P) communications link, or a machine type communications link with the synchronization platform and/or the other swappable wearable device when the circuitry determines that the swappable wearable device has been removed from the body of the individual, as in block 420. The circuitry can be further configured to communicate sync data with the synchronization platform and/or the other swappable wearable device using the communications link, as in block 430.

Figure 5:
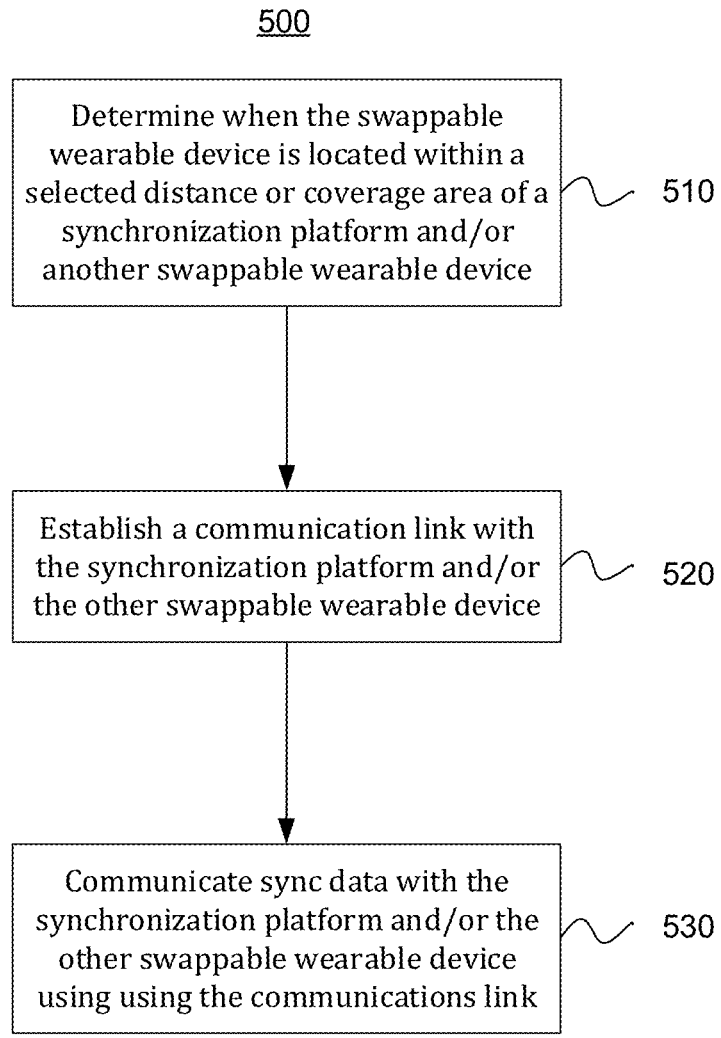
FIG. 5 depicts the functionality of circuitry of a swappable wearable device operable to transfer data with a synchronization platform in accordance with an example.

FIG. 5 shows a flow chart 500 illustrating a functionality of one embodiment of the circuitry with a swappable wearable device operable to transfer data with a synchronization platform. The functionality may be implemented as a method or the functionality may be executed as instructions on a machine, where the instructions are included on at least one computer readable medium or one non-transitory machine readable storage medium. The circuitry can be configured to determine when the swappable wearable device is located within a selected distance or coverage area of a synchronization platform and/or another swappable wearable device, as in block 510. In one example, the synchronization platform and/or the other swappable wearable device can broadcast or transmit a beacon signal within a selected coverage area, such as 5 feet, and the swappable wearable device can use the beacon signal to determine when the swappable wearable device is located within the selected distance or the coverage area of the synchronization platform and/or the other swappable wearable device.

In another embodiment, the swappable wearable device can broadcast and/or unicast a beacon signal to the synchronization platform and/or the other swappable wearable device and the synchronization platform and/or the other swappable wearable device can communicate an acknowledgement message to the swappable wearable device indicating that the swappable wearable device is located within the selected distance or the coverage area of the synchronization platform and/or the other swappable wearable device. In another embodiment, the swappable wearable device, the synchronization platform and/or the other swappable wearable device can include a radio frequency identification (RFID) tag. In one example, the swappable wearable device can include an RFID tag reader and when the swappable wearable device is within range of reading the RFID tag, the swappable wearable device can determine that the swappable wearable device is within the selected distance or the coverage area of the synchronization platform and/or the other swappable wearable device. In another example, the synchronization platform and/or the other swappable wearable device can include an RFID tag reader and when the swappable wearable device is within range of the RFID tag reader, the synchronization platform and/or the other swappable wearable device can determine that the swappable wearable device is within the selected distance or the coverage area of the synchronization platform and/or the other swappable wearable device. In this example, when the synchronization platform and/or the other swappable wearable device determines that the swappable wearable device is within the selected distance or the coverage area of the synchronization platform and/or the other swappable wearable device, the synchronization platform and/or the other swappable wearable device can send a message to the swappable wearable device indicating the swappable wearable device is within the selected distance or coverage area.

In another embodiment, the swappable wearable device can be further configured to establish a communication link, such as a cellular network communications link or a wireless network communications link, with the synchronization platform and/or the other swappable wearable device when the swappable wearable device determines that the swappable wearable device is located within a selected distance or coverage area of a synchronization platform and/or another swappable wearable device, as in block 520. The swappable wearable device can be further configured to communicate sync data with the synchronization platform and/or the other swappable wearable device using the communications link, as in block 530.

Figure 6A:
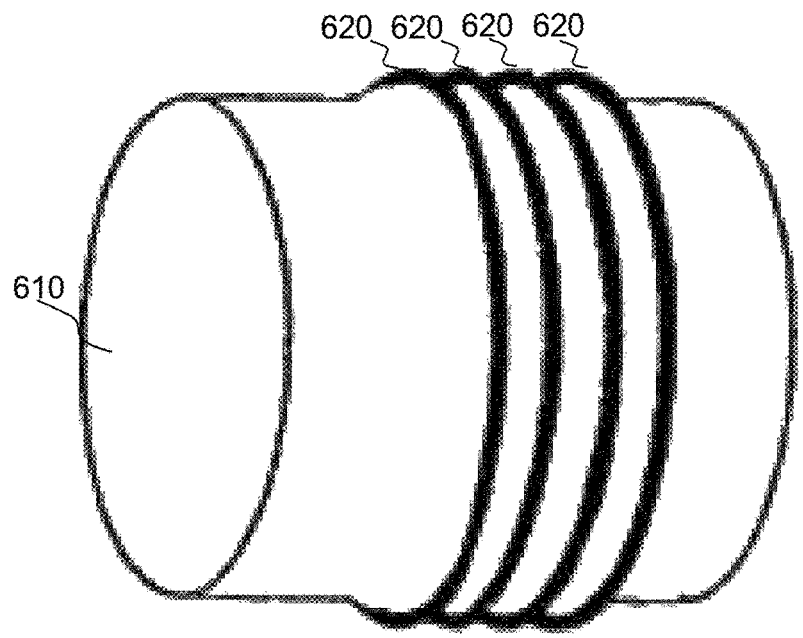
FIG. 6a depicts a synchronization platform sized and shaped as a cylindrical platform coupled to the plurality of swappable wearable devices in accordance with an example.
Figure 6B:
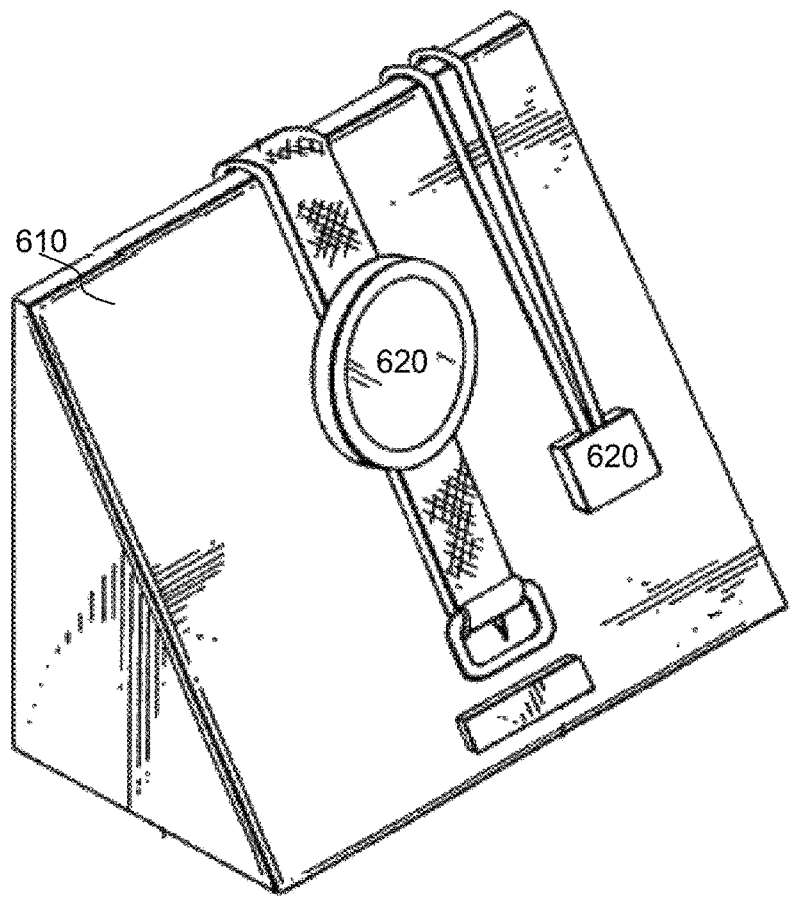
FIG. 6b depicts another exemplary embodiment of the synchronization platform sized and shaped as a podium or pedestal platform coupled to the plurality of swappable wearable devices in accordance with an example.

In one embodiment, the synchronization platform can receive sync data from a plurality of swappable wearable devices. In another embodiment, the plurality of swappable wearable device can each be used by different users. In another embodiment, the plurality of swappable wearable device can each be used the same user. FIGS. 6*a* and 6*b* depict a synchronization platform 610 and a plurality of swappable wearable devices 620. FIG. 6*a* depicts one exemplary embodiment of the synchronization platform 610 sized and shaped as a cylindrical platform coupled to the plurality of swappable wearable devices 620. FIG. 6*b* depicts another exemplary embodiment of the synchronization platform 610 sized and shaped as a podium or pedestal platform coupled to the plurality of swappable wearable devices 620.

Figure 7:
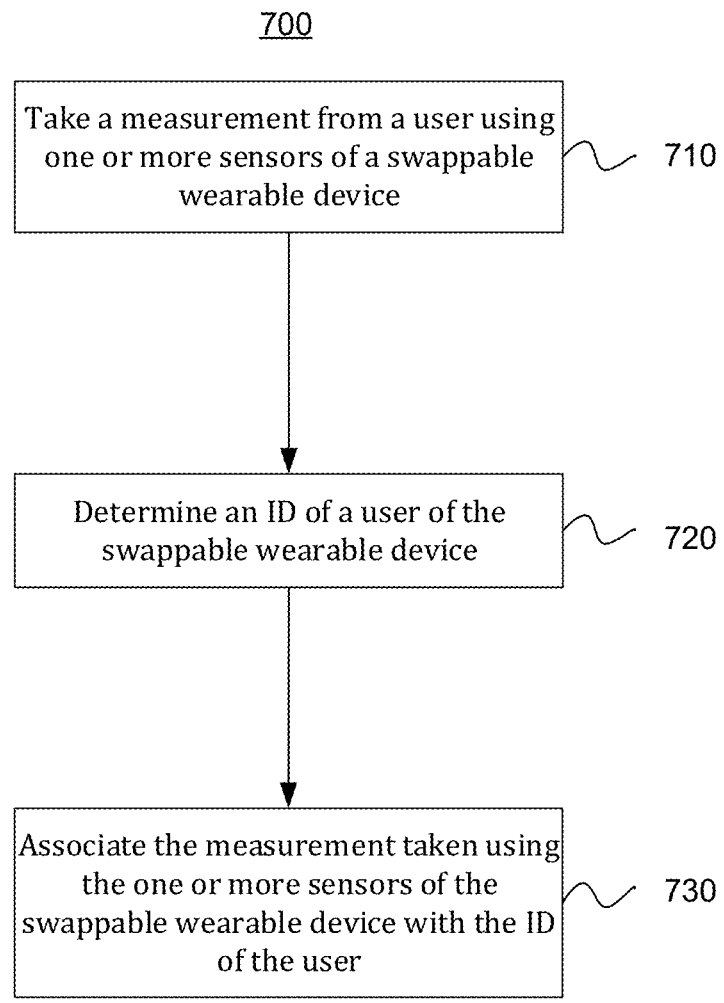
FIG. 7 depicts the functionality of circuitry of a swappable wearable device operable to associate sync data with a user in accordance with an example.

FIG. 7 shows a flow chart 700 illustrating a functionality of one embodiment of the circuitry with a swappable wearable device operable to associate sync data with a user. The functionality may be implemented as a method or the functionality may be executed as instructions on a machine, where the instructions are included on at least one computer readable medium or one non-transitory machine readable storage medium. In one embodiment, the swappable wearable device can be configured to take a measurement from a user using one or more sensors of a swappable wearable device, as in block 710. In another embodiment, the swappable wearable device can be configured to determine an identification (ID) of a user of the swappable wearable device, as in block 720. In one example, the swappable wearable device can determine the ID of the user by receiving ID information (such as a pin number or password) via a graphical user interface of the swappable wearable device and/or a device couple to the swappable device. In another example, the swappable wearable device can determine the ID of the user by taking a security measurement of the user using one or more sensors of the swappable wearable device, such as a biometric ID measurement, fingerprint, vein print, and so forth. In another example, the swappable wearable device can determine the ID of the user by comparing a current measurement of the user with a predetermined or stored measurement of the user to authenticate that the current measurement is substantially similar to the predetermined or stored measurement. In another embodiment, the swappable wearable device can be configured to associate the measurements taken using the one or more sensors of the swappable wearable device with the ID of the user. In one example, the swappable wearable device can associate the sync data of the user with a user ID, as in block 730. In another embodiment, the synchronization platform can associate the sync data with the user of the swappable wearable device.

Figure 8A:
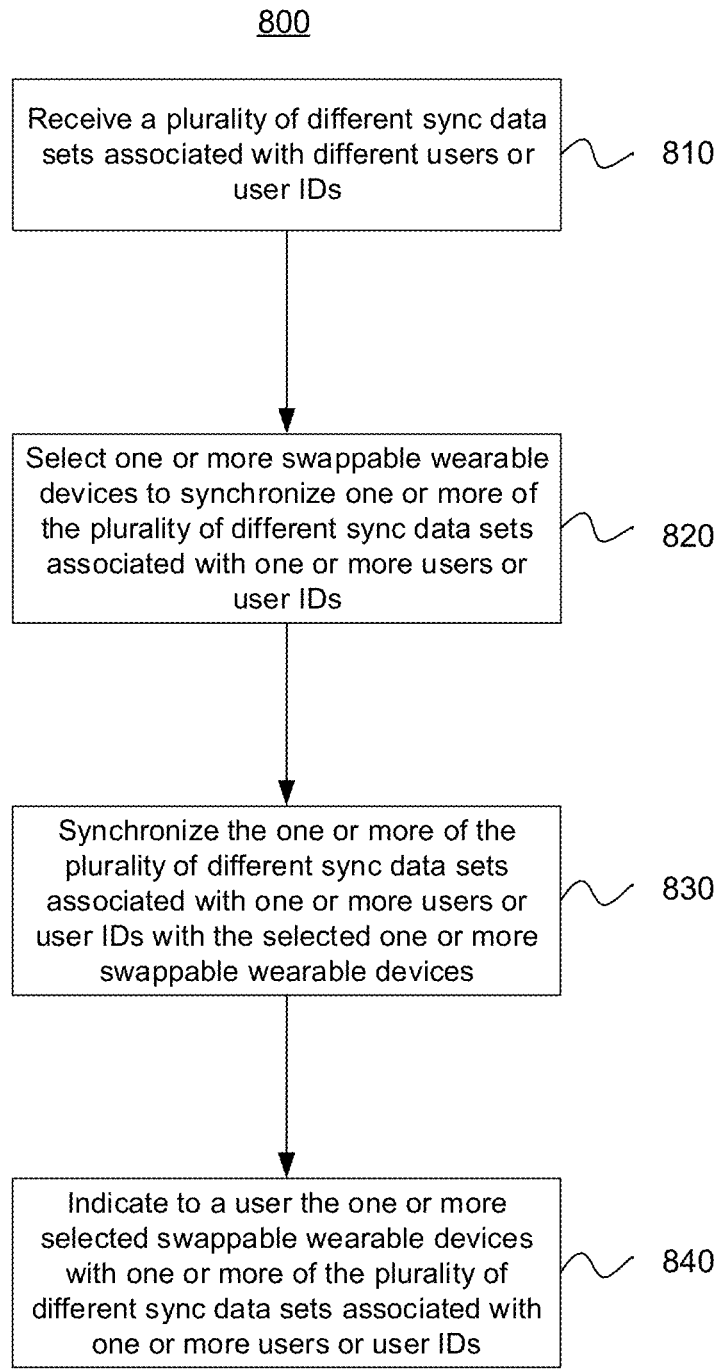
FIG. 8a depicts the functionality of circuitry of a synchronization platform operable to synchronize one or more of the plurality of different sync data sets with one or more other swappable wearable devices in accordance with an example.

FIG. 8*a* shows a flow chart 800 illustrating a functionality of one embodiment of the circuitry with a synchronization platform operable to synchronize one or more of the plurality of different sync data sets with one or more other swappable wearable devices. The functionality may be implemented as a method or the functionality may be executed as instructions on a machine, where the instructions are included on at least one computer readable medium or one non-transitory machine readable storage medium. In one embodiment, the synchronization platform can be configured to receive a plurality of different sync data sets associated with different users or user IDs, as in block 810. In one example, the synchronization platform can receive a plurality of sync data sets from a plurality of different swappable wearable devices, such as multiple players on a sports team or multiple patients on a hospital floor. In another embodiment, the synchronization platform can be configured to select one or more swappable wearable devices to synchronize one or more of the plurality of different sync data sets associated with one or more users or user IDs, as in block 820. In another embodiment, the synchronization platform can be configured to synchronize the one or more of the plurality of different sync data sets associated with one or more users or user IDs with the selected one or more swappable wearable devices, as in block 830. In one example, the selected one or more swappable wearable devices can be one or more swappable wearable devices not currently being used by a user.

In one embodiment, the synchronization platform can be configured to indicate to a user the one or more selected swappable wearable devices with one or more of the plurality of different sync data sets associated with one or more users or user IDs, as in block 840. In another embodiment, the one or more selected swappable wearable devices can indicate to the user that the swappable wearable device received the sync data from the synchronization platform. In another embodiment, the synchronization platform and/or the one or more selected wearable devices can include an auditory indicator to indicate to the user the one or more swappable wearable devices that received the sync data. In one embodiment, the auditory indicator can be a speaker, display, vibrator, and so forth. In one example, the synchronization platform and/or the selected swappable wearable device can use a display to indicate the selected swappable wearable device to use. In another example, the display can be a liquid emitting diode (LED) display and/or liquid crystal display (LCD) configured to display a selection indicator. In one embodiment, the currently used swappable wearable device and/or the synchronization platform can synchronize the sync data to swappable wearable devices of each of the users when each user is within a selected distance of the synchronization platform. In another embodiment, a graphical user interface of the currently used swappable wearable device can receive a command to synchronize the sync data with the selected swappable wearable device.

In one example, when a selected user, such as a player or a patient, desires to switch a swappable wearable device currently in use with another swappable wearable device (such as if a battery of the swappable wearable device in current use is nearly depleted), the synchronization platform can receive a sync data set for the selected player or selected patient and synchronize the sync data set with the other swappable wearable device. When the sync data set is synchronized with the other swappable wearable device, the selected player or the selected patient can switch the current swappable wearable device for the other swappable wearable device.

In one configuration, the swappable wearable device can store a plurality of different data sets associated with different users. In one example, the swappable wearable device can be configured to authenticate an ID of a selected user and recall a data set for the selected user. In this example, when the swappable wearable device recalls the data set for the selected user, the swappable wearable device can take measurements using one or more sensor coupled to the swappable wearable device and continue to add measurement information to the data set for the selected user.

One advantage of the synchronization platform receiving sync data sets for a plurality of users is that a plurality of swappable wearable devices can be available for switching when one or more of the plurality of users desires to switch a currently used swappable wearable device. In one example, a plurality of players on a sports team can use a plurality of swappable wearable devices to monitor cardiac and hydration information and when multiple players of the plurality of players desire to switch swappable wearable devices, each of the multiple players of the plurality of players can switch the swappable wearable devices with other swappable wearable devices. In one embodiment, the synchronization platform can select a swappable wearable device for one of the plurality of users to switch the swappable wearable device. In this embodiment, when the synchronization platform selects a swappable wearable device, the synchronization platform can then synchronize sync data of the swappable wearable device with the selected swappable wearable device. In one embodiment, the synchronization platform and/or the selected swappable wearable device can indicate to the user the selected swappable wearable device to switch with the swappable wearable device with.

Figure 8B:
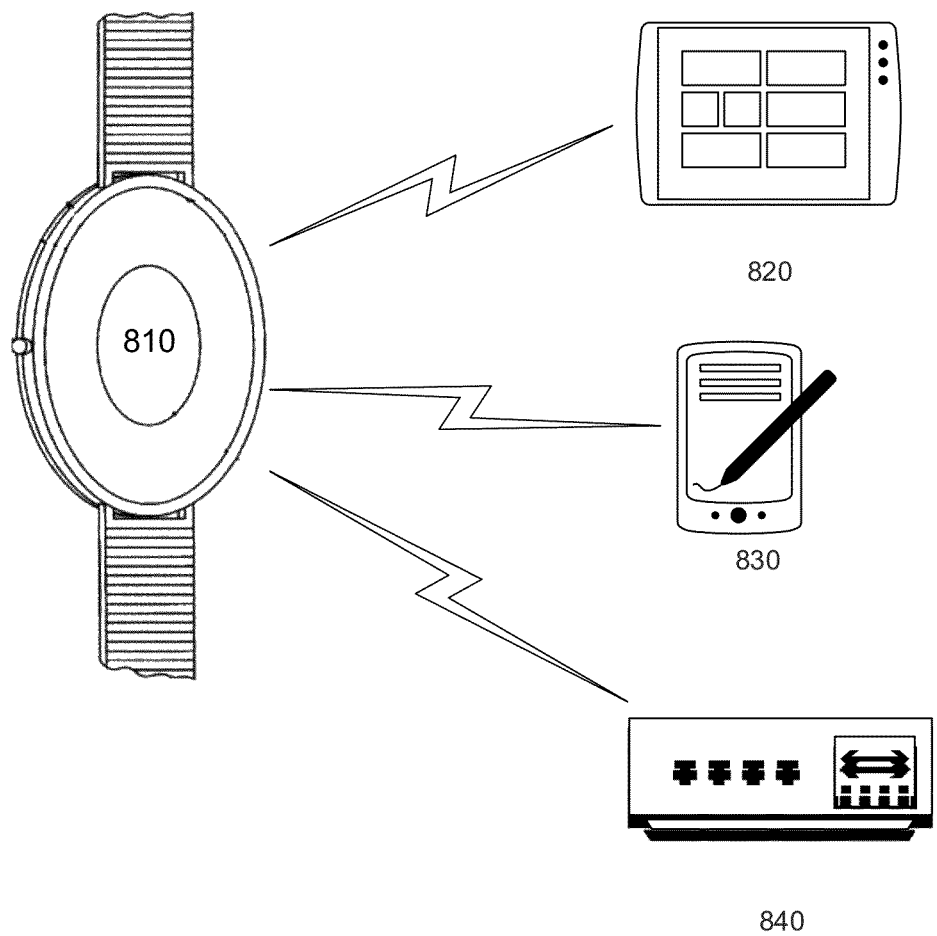
FIG. 8b a synchronization platform and/or a swappable wearable device configured to communicate data, such as sync data, with one or more other devices in accordance with an example.

FIG. 8b depicts a synchronization platform and/or a swappable wearable device 810 configured to communicate data, such as sync data, with one or more other devices 820, 830, and/or 840. In one embodiment, the other devices can be non-swappable devices and/or non-wearable devices, such as a bathroom scale or a bed scale 820, a medical device 830, and/or a continuous positive airway pressure (CPAP) device 840. In another embodiment, the synchronization platform and/or the swappable wearable device can store and/or analyze the data received from the one or more other devices separately from data of the synchronization platform and/or the swappable wearable device. In another embodiment, the synchronization platform and/or the swappable wearable device can aggregate the data received from the one or more other devices with the sync data of the synchronization platform and/or the swappable wearable device. In another embodiment, the synchronization platform and/or the swappable wearable device can store, synchronize, and/or analyze the aggregated data of the one or more other devices and the synchronization platform and/or the swappable wearable device.

Figure 9:
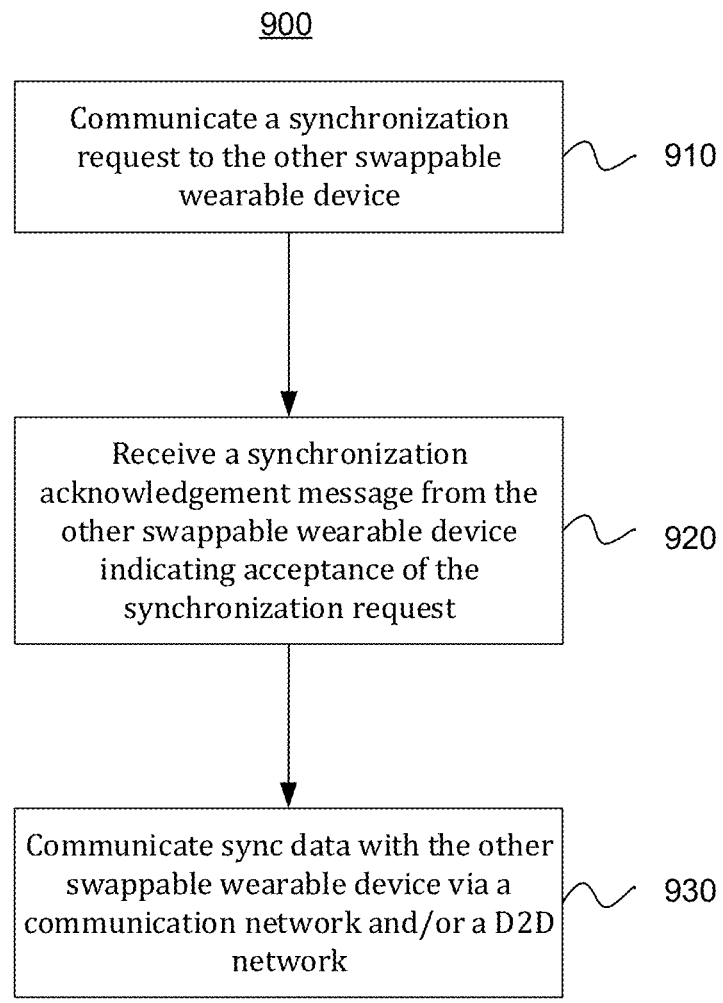
FIG. 9 depicts the functionality of circuitry of a swappable wearable device and/or a synchronization platform operable to communicate sync data with another swappable wearable device in accordance with an example.

FIG. 9 shows a flow chart 900 illustrating a functionality of one embodiment of the circuitry with a swappable wearable device and/or a synchronization platform operable to communicate sync data with another swappable wearable device. The functionality may be implemented as a method or the functionality may be executed as instructions on a machine, where the instructions are included on at least one computer readable medium or one non-transitory machine readable storage medium. In one embodiment, the swappable wearable device and/or the synchronization platform can be configured to communicate a synchronization request to the other swappable wearable device, as in block 910. In another embodiment, the swappable wearable device and/or the synchronization platform can be configured to receive a synchronization acknowledgement message from the other swappable wearable device indicating acceptance of the synchronization request, as in block 920. In one example, the synchronization acknowledgement message can include authentication information, such as a frequency to communicate sync data with the other swappable wearable device, a security identification information, encryption information, and so forth. In another embodiment, the swappable wearable device and/or the synchronization platform can be configured to communicate sync data with the other swappable wearable device via a communication network and/or a device to device (D2D) network, as in block 930.

In one embodiment, the synchronization platform can store sync data received from a swappable wearable device on a non-transitory computer readable medium. In another embodiment, the synchronization platform can communicate sync data to another computing device, such as a server or cloud service. In another embodiment, the synchronization platform and/or the swappable wearable device can store sync data for a selected period of time, such as a selected number of minutes, hours, days, weeks, months, or years.

Figure 10:
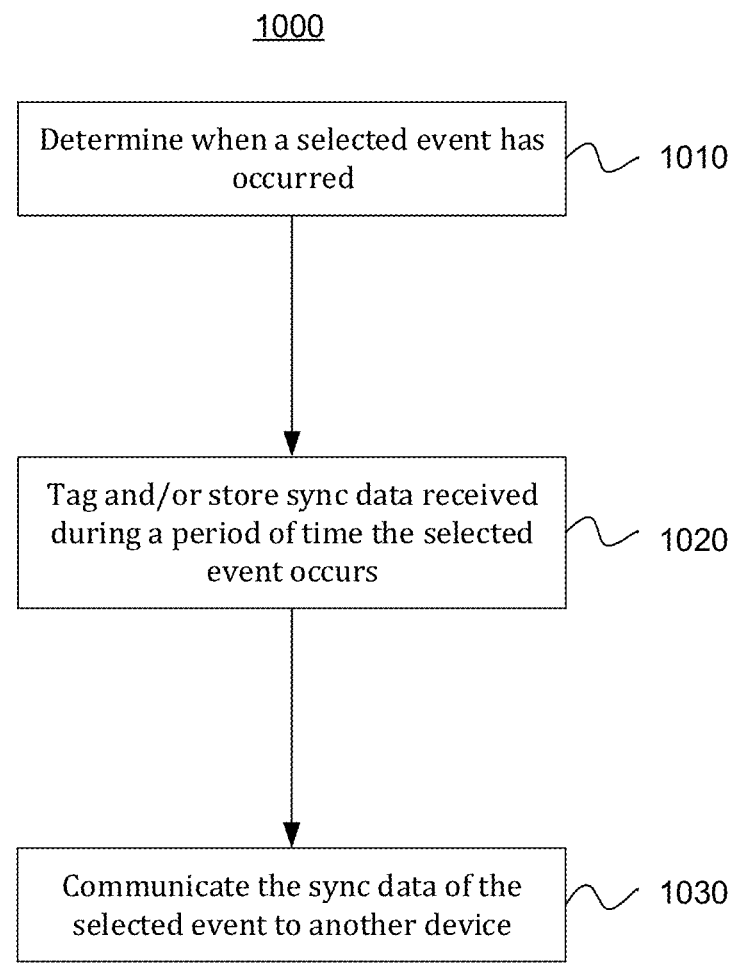
FIG. 10 depicts the functionality of circuitry of a swappable wearable device and/or a synchronization platform operable to communicate sync data with another device when a selected event occurs in accordance with an example.

FIG. 10 shows a flow chart 1000 illustrating a functionality of one embodiment of the circuitry with a swappable wearable device and/or a synchronization platform operable to communicate sync data with another device when a selected event occurs. The functionality may be implemented as a method or the functionality may be executed as instructions on a machine, where the instructions are included on at least one computer readable medium or one non-transitory machine readable storage medium. In one embodiment, the swappable wearable device and/or the synchronization platform can be configured to determine when a selected event has occurred, as in block 1010. In one embodiment, the swappable wearable device and/or the synchronization platform can determine when a selected event has occurred using a sensor coupled to the swappable wearable device. In one example, the selected event can include: a medical event, such as a cardiac episode or dehydration event; sleeping periods of the user; exercise periods of the user; and so forth. In one embodiment, the selected event can be a change in the sync data that exceeds a selected data set threshold range.

In another embodiment, the swappable wearable device and/or the synchronization platform can be configured to tag and/or store sync data received during a period of time the selected event occurs, as in block 1020. In one example, the swappable wearable device and/or the synchronization platform can receive the sync data from a sensor coupled to the swappable wearable device or from another swappable wearable device. In another example, the swappable wearable device and/or the synchronization platform can tag and/or store sync data, such as measurement data, when there is a change in a trend of the sync data, such as a change in blood pressure measurement data or hydration level data. In another embodiment, the swappable wearable device and/or the synchronization platform can be configured to communicate the sync data of the selected event to another device, as in block 1030. In one embodiment, the other device can be a different swappable wearable device and/or another synchronization platform. In another embodiment, the swappable wearable device and/or the synchronization platform can be configured to communicate the sync data of the selected event to another device when the selected event has ceased occurring.

In one example, the swappable wearable device can monitor a selected medical condition of a user, such as blood pressure or a hydration level. In this example, when the measurement data is substantially unchanged or constant the swappable wearable device may not communicate the measurement data. However, when there is a change in the measurement data information, such as a change in that exceeds a selected data range threshold, the swappable wearable device can communicate the measurement data to the synchronization platform. In one embodiment, when the synchronization platform receives the measurement data, the synchronization platform can communicate the information to another swappable wearable device and/or another device (such as a server or cloud storage device).

Figure 11:
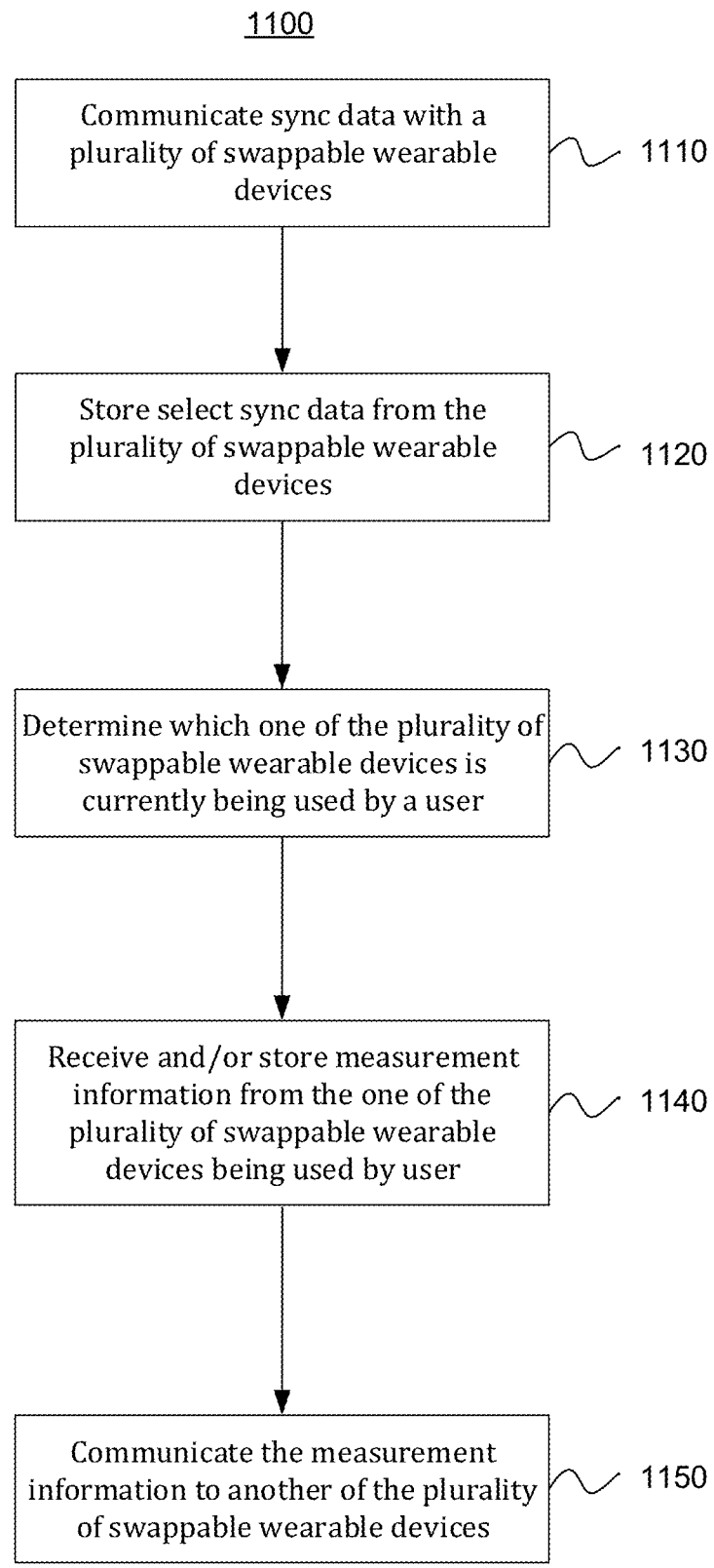
FIG. 11 depicts the functionality of circuitry of a swappable wearable device and/or a synchronization platform operable to communicate sync data with a plurality of other swappable wearable devices in accordance with an example.

FIG. 11 shows a flow chart 1100 illustrating a functionality of one embodiment of the circuitry with a swappable wearable device and/or a synchronization platform operable to communicate sync data with a plurality of other swappable wearable devices. The functionality may be implemented as a method or the functionality may be executed as instructions on a machine, where the instructions are included on at least one computer readable medium or one non-transitory machine readable storage medium. In another embodiment, the swappable wearable device and/or the synchronization platform can be configured to communicate sync data with a plurality of swappable wearable devices, as in block 1110.

In one embodiment, the swappable wearable device and/or the synchronization platform can be configured to store select sync data from the plurality of swappable wearable devices, as in block 1120. In one example, the sync data can include baseline information, user preference information, medical record information, and so forth. In another embodiment, when the plurality of swappable wearable devices are in communication with the swappable wearable device and/or the synchronization platform, the swappable wearable device, the synchronization platform, and/or one or more of the plurality of swappable wearable devices can be configured to determine which one of the plurality of swappable wearable devices is currently being used by a user, as in block 1130. In another embodiment, when the swappable wearable device, the synchronization platform, and/or one or more of the plurality of swappable wearable devices determines which one of the plurality of swappable wearable devices is currently being used by the user, the swappable wearable device and/or the synchronization platform can be configured to receive and/or store measurement information from the one of the plurality of swappable wearable devices being used by user, as in block 1140. In another embodiment, the swappable wearable device and/or the synchronization platform can be configured to communicate the measurement information to another of the plurality of swappable wearable devices, as in block 1150.

In one example, the swappable wearable device currently being used by a user can take measurements using one or more sensors of the swappable wearable device and communicate the measurement information to the synchronization platform. In this example, the synchronization platform can communicate the measurement data to the remaining plurality of swappable wearable devices to synchronize the data between the plurality of swappable wearable devices. In another embodiment, when the synchronization platform and/or one of the plurality of swappable wearable devices determines which one of the plurality of swappable wearable devices is currently being used by a user, the one of the plurality of swappable wearable devices being used by user can communicate measurement information directly to one or more of the plurality of swappable wearable devices.

In one embodiment, a plurality of swappable wearable devices can take measurements using selected sensors at substantially the same time. In one example, a user can wear a first swappable wearable device (such as a swappable wearable device to monitor hydration) and a second swappable wearable device (such as a swappable wearable device to monitor blood pressure) at the same time. In another embodiment, the first swappable wearable device can communicate sync data, such as measurement data, directly with the second swappable wearable device while the user is using the first swappable wearable device and the second swappable wearable device at substantially the same time. In another embodiment, the first swappable wearable device can communicate sync data, such as measurement data, indirectly with the second swappable wearable device via a synchronization plate while the user is using the first swappable wearable device and the second swappable wearable device at substantially the same time. In one embodiment, one or more of the plurality of swappable wearable devices and/or the synchronization plate can aggregate the sync information (such as measurement information) from the plurality of swappable wearable devices taking measurements at substantially the same time.

In one embodiment, the synchronization platform can provide energy to one or more of the swappable wearable devices. In one example, the synchronization platform and the one or more swappable wearable devices can include electrical contacts used to transfer power between the synchronization platform and the one or more swappable wearable devices. In another embodiment, the synchronization platform can provide power to one or more of the swappable wearable device via a wireless power transfer.

Figure 12:
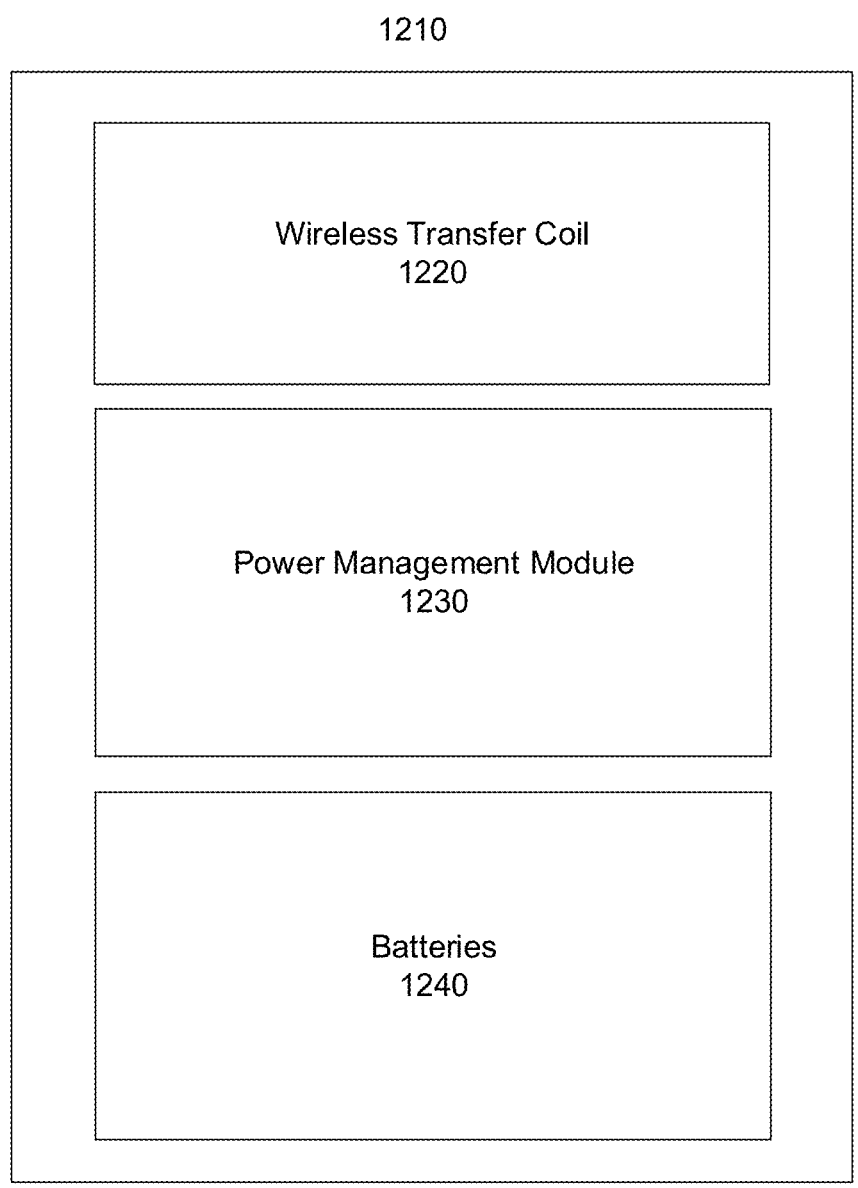
FIG. 12 illustrates a swappable wearable device and/or a synchronization platform in accordance with an example.

FIG. 12 illustrates a swappable wearable device and/or a synchronization platform 1210. FIG. 12 further illustrates that the swappable wearable device and/or the synchronization platform 1210 can include a wireless transfer coil 1220 and a management module 1230. In one example, the management module 1230 of the swappable wearable device and/or the synchronization platform 1210 can convert energy received at the wireless transfer coil 1220 from an energy source, such as an alternating current (AC) energy outlet, to a selected current level, a selected voltage level, and/or a selected wattage level. In another embodiment, the swappable wearable device and/or the synchronization platform 1210 can include one or more batteries 1240, such as rechargeable batteries. In one embodiment, the wireless transfer coil can be a transmitting coil and/or a receiving coil.

Figure 13:
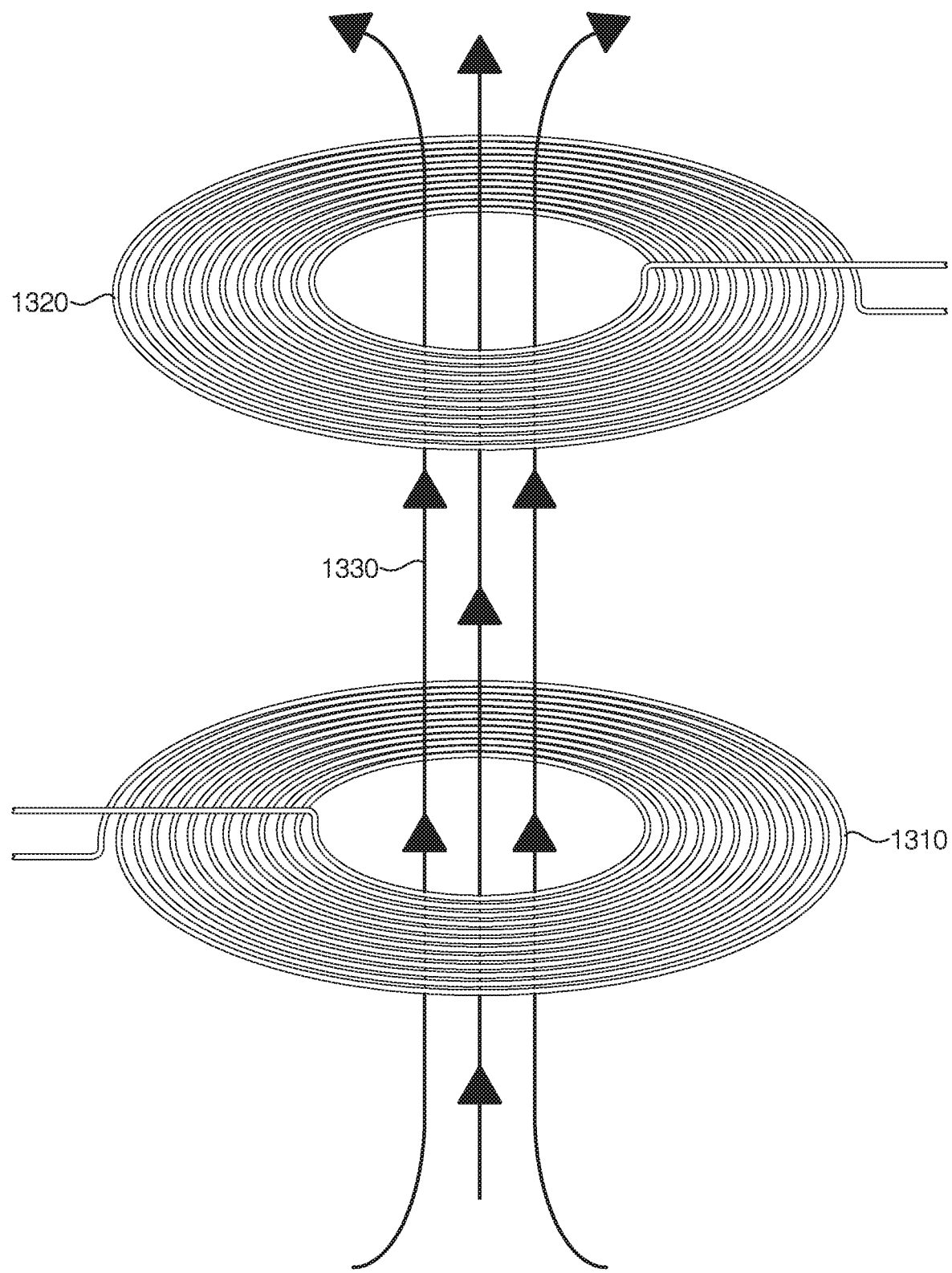
FIG. 13 illustrates an example of transferring energy or data between a plurality of wireless transfer coils in accordance with an example.

FIG. 13 illustrates an example of transferring energy or data between a plurality of wireless transfer coils 1310 and 1320. FIG. 13 further illustrates that a first wireless transfer coil 1310 can be a transmitting coil and a second wireless transfer coil 1320 can be a receiving coil. In one embodiment, energy and/or data can be transferred from the transmitting coil to the receiving coil by coupling the transmitting coil with the receiving coil to enable the energy or data to be transferred over a gap or distance. In one example, wireless energy can be transferred by generating a magnetic field 1330 at the transmitting coil and positioning the receiving coil within the magnetic field to induce a current at the receiving coil. In one embodiment, the magnetic field can be an electromagnetic field. The process of inducing a current at the receiving coil is referred to as coupling the receiving coil to the transmitting coil. In one embodiment, the wireless transfer coil coupling for wireless energy or data transfer can be a magnetic induction coupling. In another embodiment, the wireless transfer coil coupling for wireless energy transfer can be a magnetic resonant coupling.

In one embodiment, the transmitting coil can be a transmitting induction coil and the receiving coil can be a receiving induction coil. The swappable wearable device and/or the synchronization platform can use a magnetic field to transfer energy between the transmitting coil coupled to a first object (such as a synchronization platform) and a receiving coil of a second object (such as a swappable wearable device) without any direct contact between the transmitting coil and the receiving coil, e.g. inductive coupling.

In one example, when the transmitting coil and the receiving coil are within a threshold proximity distance, the transmitting coil and the receiving coil can couple to form an electric transformer. In one embodiment, current from the receiving coil can be transferred to a battery of the swappable wearable device or the synchronization platform. In one embodiment, an impedance of the transmitting coil can be substantially matched with an impedance of the receiving coil.

In one embodiment, the transmitting coil can be a transmitting resonant coil and the receiving coil can be a receiving resonant coil. A wireless resonant transfer can be a resonant transmission of energy or data between at the transmitting coil and the receiving coil. In another embodiment, the transmitting coil and the receiving coil can be tuned to resonate at a same frequency or a substantially same frequency.

In one example, resonant transmission of wireless energy can occur when the transmitting coil and the receiving coil are constructed to resonate at the same frequency or approximately the same frequency. The transmitting coil can be configured to oscillate current at a resonant frequency of the receiving coil to transfer energy and/or data. The oscillating current of the transmitting coil can generate an oscillating magnetic field at the selected resonant frequency of the receiving coil. When the receiving coil is positioned adjacent to the oscillating magnetic field and constructed to operate at the same frequency or substantially the same frequency as the transmitting coil, the receiving coil can receive energy and/or data from the oscillating magnetic field.

Figure 14:
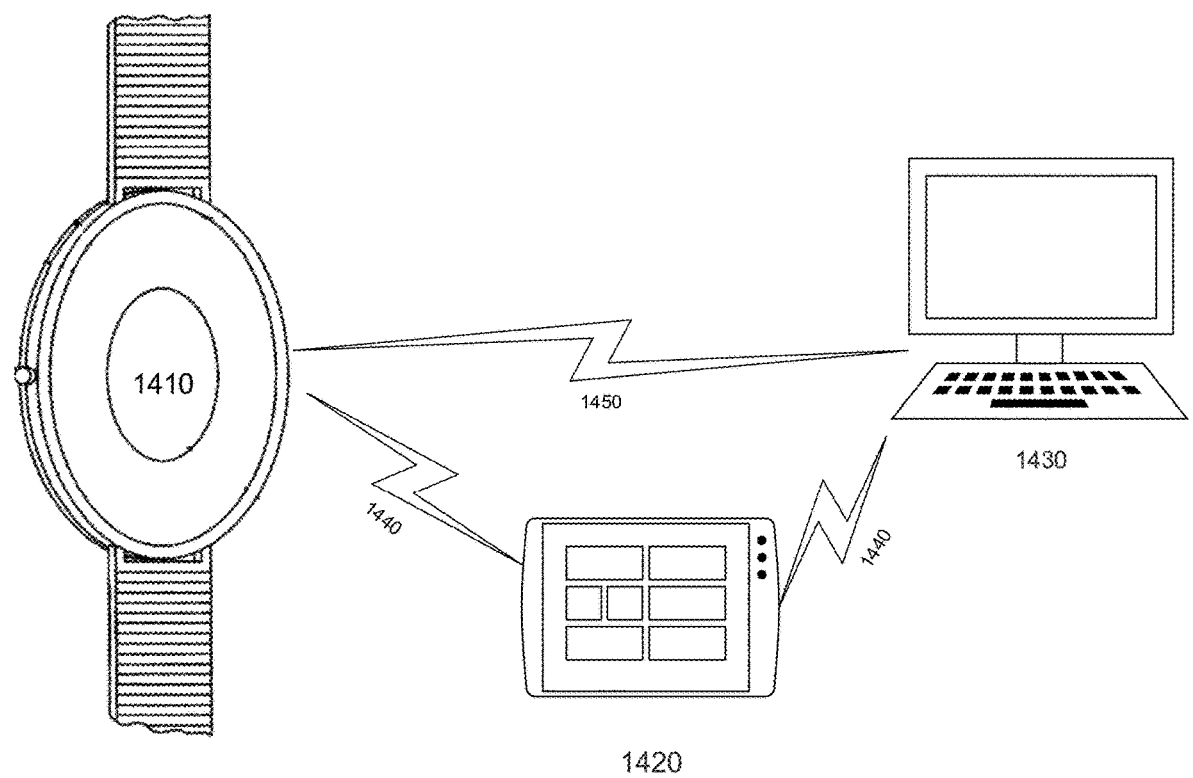
FIG. 14 depicts the functionality of circuitry of a synchronization platform and/or a swappable wearable device operable to communicate sync data to a computing device in accordance with an example.

FIG. 14 illustrates a synchronization platform and/or a swappable wearable device 1410 operable to communicate sync data to a computing device 1430, such as a server. In one example, the synchronization platform and/or the swappable wearable device 1410 can communicate sync data directly to the computing device 1430 using a communications connection 1450 of a communications network. In another example, the synchronization platform and/or the swappable wearable device 1410 can indirectly communicate the sync data to the computing device 1430 using another synchronization platform or another swappable wearable device 1420 along communication connections 1440. In another embodiment, the computing device 1430 can be a medical facility server or a device in communication with a medical facility server. In another embodiment, the computing device 1430 can be a laptop, tablet, or smartphone. In one example, the medical facility server can receive the sync data and provide the sync data to a medical professional, such as a doctor. In one embodiment, another computing device coupled to the medical facility server can include a display or a graphical user interface that can be configured to display the sync data to the medical professional. In another embodiment, the medical facility server can communicate the sync data to a computing device used by the medical professional, such as a smartphone or tablet.

FIG. 14 further illustrates that the synchronization platform and/or a swappable wearable device 1410 can receive selected data or information, such as sync data or other information, from the computing device 1430. In one example, the synchronization platform and/or a swappable wearable device 1410 can receive selected data or information for a user of the synchronization platform and/or a swappable wearable device 1410 from a medical facility server or a server in communication with a medical facility server.

In one embodiment, the selected data or information can include setting information for the synchronization platform and/or a swappable wearable device 1410. In one example, the setting information can include: measurement data threshold ranges, measurement data threshold values, measurement event triggering values, and so forth. In another example, the selected information can include: medical information of the user of a swappable wearable device, such as medical condition information of the user, medication regiment information, exercise regiment information, medical risk information, medication taking reminders, medication re-order reminders and so forth. In another embodiment, the swappable wearable device and/or the synchronization platform 1410 can provide a sensory indication (such as a visual, auditory, and/or touch indication) communicating the selected data or information to the user. In one example, the swappable wearable device and/or the synchronization platform 1410 can display a reminder for a user to exercise, take medication, re-order medication, rehydrate, and so forth.

In one embodiment, the synchronization platform can analyze received sync information and/or stored sync data (such as measurement information) to determine selected states or conditions, such as medical conditions, physiological states, and so forth of the user of the swappable wearable device. In another embodiment, the synchronization platform can aggregate sync data received from a plurality of swappable wearable devices. In another embodiment, the synchronization platform can aggregate current sync information received from one or more swappable wearable device or other synchronization platform with previous sync data stored on the synchronization platform or a device in communication with the synchronization platform. In another embodiment, the synchronization platform can analyze the aggregated sync data.

In one configuration, the synchronization platform can communicate other information to one or more swappable wearable devices. For example, the synchronization platform can receive software and/or firmware update information and relay the software and/or firmware update to the one or more swappable wearable devices. In one embodiment, the synchronization platform can communicate the other information to the one or more swappable wearable devices when the one or more swappable wearable devices receive energy (such as wired energy or wireless energy) from the synchronization platform. In another embodiment, the synchronization platform can communicate the other information to a currently used swappable wearable device when the user replaces the swappable wearable device with another swappable wearable device.

Figure 15:
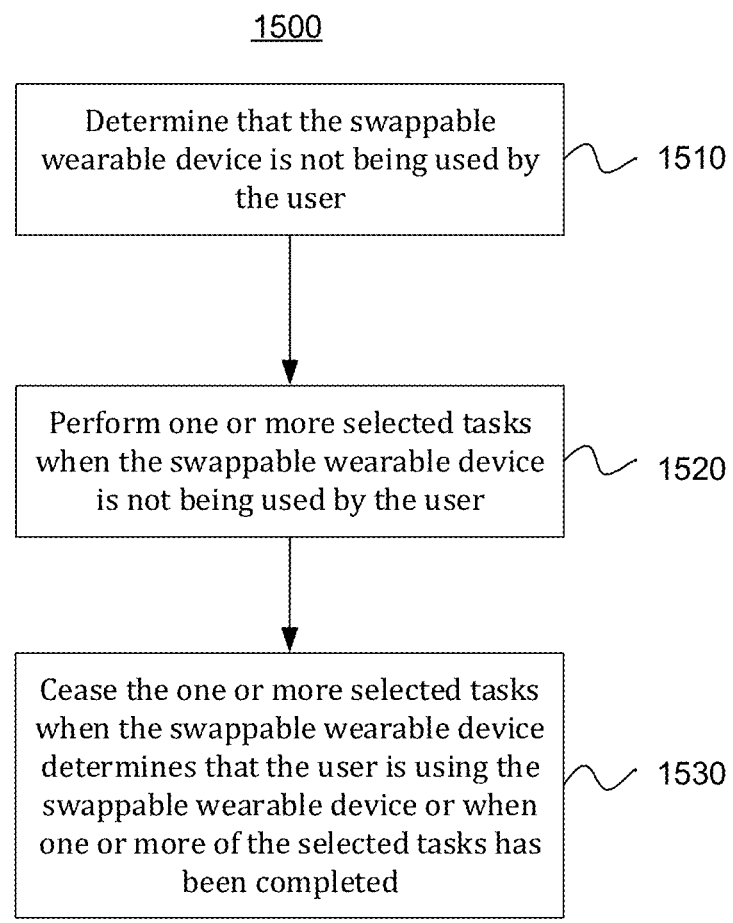
FIG. 15 depicts the functionality of circuitry of a swappable wearable device and/or a synchronization platform operable to perform one or more selected tasks in accordance with an example.

FIG. 15 shows a flow chart 1500 illustrating a functionality of one embodiment of the circuitry with a swappable wearable device and/or a synchronization platform operable to perform one or more selected tasks. The functionality may be implemented as a method or the functionality may be executed as instructions on a machine, where the instructions are included on at least one computer readable medium or one non-transitory machine readable storage medium. In one embodiment, the swappable wearable device can be configured to determine that the swappable wearable device is not being used by the user, as in block 1510. In one example, the swappable wearable device can determine that the user is using another swappable wearable device to collect sync data. In another embodiment, the swappable wearable device can be configured to perform one or more selected tasks when the swappable wearable device is not being used by the user, as in block 1520. In one embodiment, the selected tasks can include: receiving software applications from another device or application server, receiving power to recharge a battery of the swappable wearable device, receiving repairs, receiving replacement parts, updating firmware and/or software of the swappable wearable device, communicating sync data with the synchronization platform and/or other swappable wearable devices, and so forth.

In another embodiment, the swappable wearable device can cease the one or more selected tasks when the swappable wearable device determines that the user is using the swappable wearable device or when one or more of the selected tasks have been completed, as in block 1530. In one embodiment, the one or more selected tasks can be prioritized according to selected criteria and the swappable wearable device can complete the tasks in order of priority. In one example, the selected criteria include: a predetermined priority order, an amount of time the task will take to complete, an amount of time the swappable wearable device estimates that the swappable wearable device will not be used by the user, and so forth. One advantage of the swappable wearable device performing the selected tasks while the user is not using the swappable wearable device is to minimize the amount of time that a user is not being monitored because of the selected tasks. Another advantage of the swappable wearable device performing the selected tasks while the user is not using the swappable wearable device is to minimize a power consumed and processing power used by the swappable wearable device while performing the selected tasks.

In one embodiment, the synchronization platform can receive sync data, such as user information, from a computing device and send the user information to one or more of the swappable wearable devices. In one example, a user of the synchronization platform can use a graphical user interface of the computing device (such as a smartphone or tablet) coupled to the synchronization platform to receive user information. In another example, the synchronization platform can communicate the user information to the swappable wearable device. The synchronization platform can send the user information to the swappable wearable device to select initial user information or update current user information. In one embodiment, the user information can include: gender, height, weight, age, health conditions, medical conditions, medication regiments, sensor baseline information, selected swappable wearable device settings, and so forth. In another embodiment, the swappable wearable device can receive the sync data (such as the user information) directly from the computing device or from the computing device via the communications network. In another embodiment, the computing device can be coupled to the swappable wearable device and the swappable wearable device can receive the sync data (such as the user information) directly from the coupled computing device.

Figure 16:
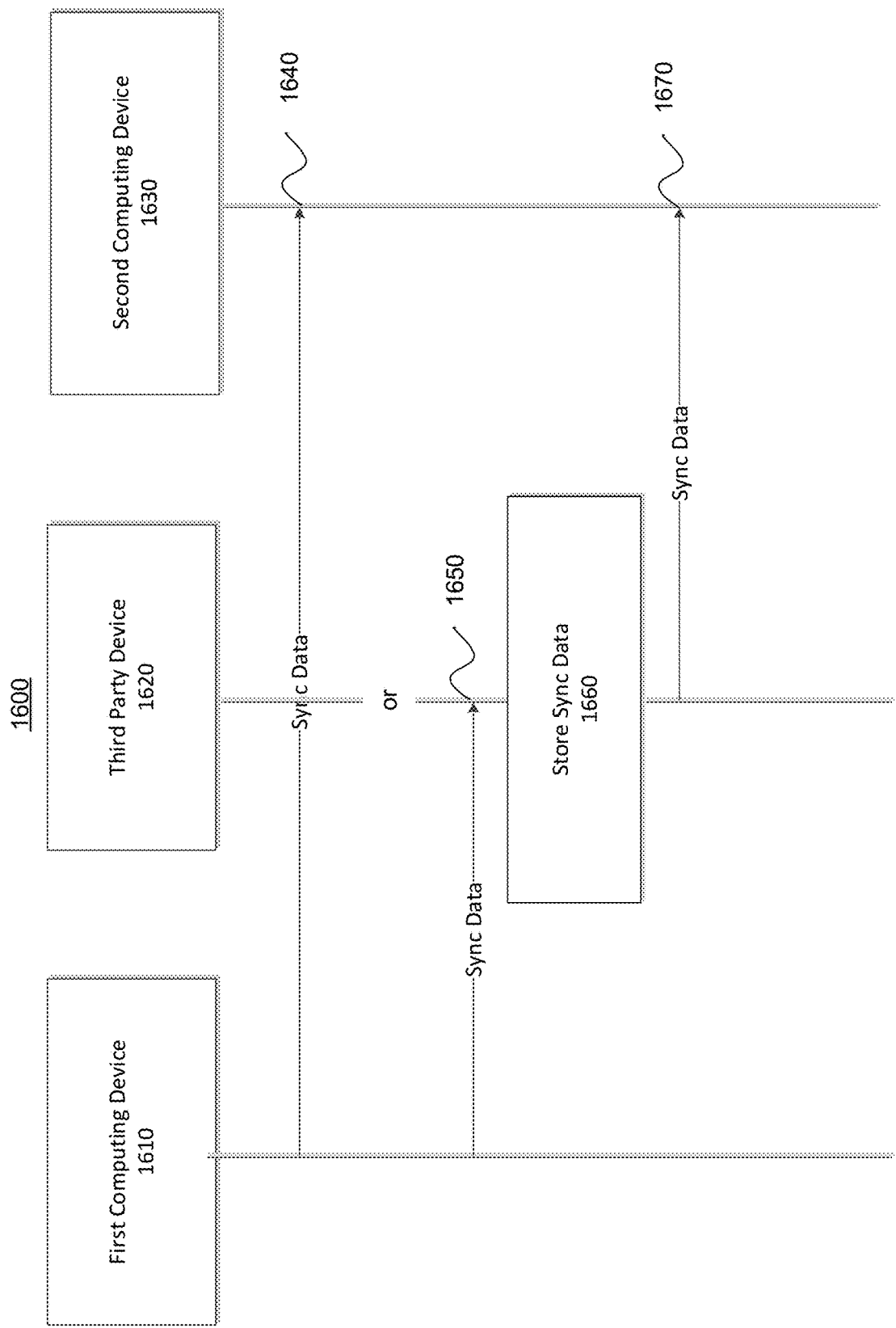
FIG. 16 depicts the functionality of circuitry of a first computing device located at a first location operable to communicate sync data to a second computing device located at a second location in accordance with an example.

FIG. 16 uses a flow chart 1600 to illustrate the functionality of one embodiment of a first computing device 1610, such as a first synchronization platform or a first swappable wearable device, located at a first location operable to communicate sync data to a second computing device 1630, such as a second synchronization platform or a second swappable wearable device, located at a second location. The functionality may be implemented as a method or the functionality may be executed as instructions on a machine, where the instructions are included on at least one computer readable medium or one non-transitory machine readable storage medium. In one example, the first computing device 1610 can communicate the sync data directly to the second computing device 1630 via a cellular communication network or a wireless communications network, as in block 1640. In another example, the first computing device 1610 can communicate the sync data indirectly to the second computing device 1630 via a third party device 1620, such as a third party server or a cloud server.

In this example, the first computing device 1610 can communicate the sync data to the third party device 1620, as in block 1650. The third party device 1620 can store the sync data, as in block 1660. The second computing device 1630 can receive the sync data from the third party device 1620, as in block 1670. In one embodiment, the first computing device 1610 can communicate the sync data to the third party device 1620 at a first selected time and the second computing device 1630 can receive the sync data at a second selected time. In one example, a user of a swappable wearable device can have a first synchronization platform located at a user's home and the user can have a second synchronization platform located at a hotel room of a vacation location of the user. In this example, the second synchronization platform located at the hotel can receive sync data from the first synchronization platform located at the user's home. Additionally, the second synchronization platform can relay the sync data from the first synchronization platform to a swappable wearable device that the user is using while at the vacation location.

Figure 17:
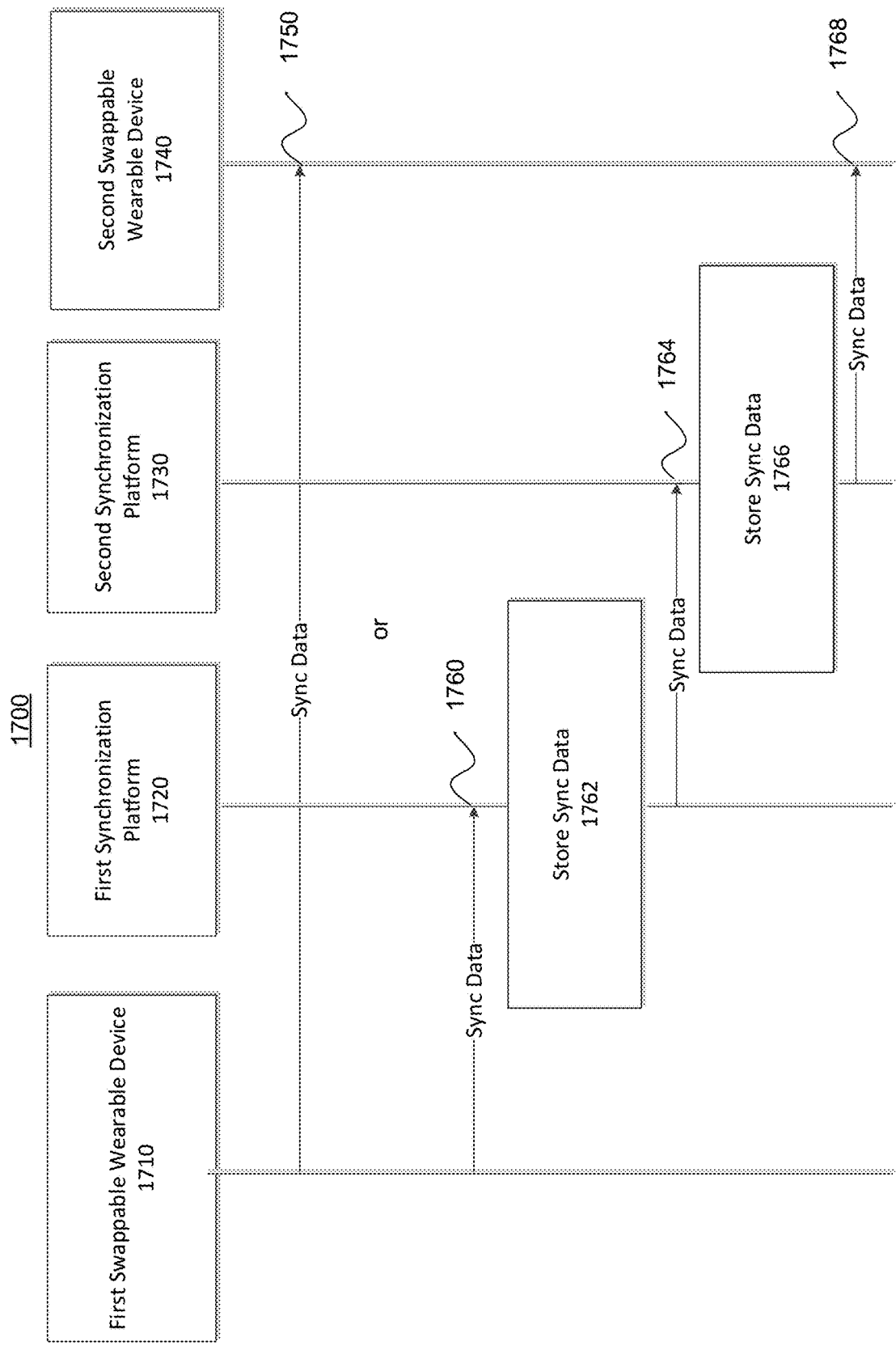
FIG. 17 depicts the functionality of circuitry of a first swappable wearable device located at a first location operable to communicate sync data to a second swappable wearable device in accordance with an example.

FIG. 17 uses a flow chart 1700 to illustrate the functionality of one embodiment of a first swappable wearable device 1710 located at a first location operable to communicate sync data to a second swappable wearable device 1740. The functionality may be implemented as a method or the functionality may be executed as instructions on a machine, where the instructions are included on at least one computer readable medium or one non-transitory machine readable storage medium. In one example, first swappable wearable device 1710 can communicate the sync data directly to the second swappable wearable device 1740 via a cellular communication network or a wireless communications network, as in block 1750.

In another example, the first swappable wearable device 1710 can communicate the sync data indirectly to the second swappable wearable device 1740. In this example, the first swappable wearable device 1710 can communicate the sync data to a first synchronization platform 1720, as in block 1760. In one embodiment, the first synchronization platform 1720 can store the sync data, as in block 1762. In another embodiment, the first synchronization platform 1720 can communicate the sync data to a second synchronization platform 1730, as in block 1764. In another embodiment, the second synchronization platform 1730 can store the sync data, as in block 1766. In another embodiment, the second synchronization platform 1730 can communicate the sync data to the second swappable wearable device 1740, as in block 1768. One advantage of the first swappable wearable device 1710 located at a first location communicating sync data to a second swappable wearable device 1740 is that a user can have the second swappable wearable device 1740 for use while on vacation (such as if the user forgot to bring the first swappable wearable device on vacation).

In one example, a medical facility can have a first synchronization platform located at a surgical room and the medical facility can have a second synchronization platform located at a recovery room of the medical facility. In this example, the medical facility can provide a patient with a surgery swappable wearable device at the surgical room, before a medical procedure, that is configured to monitor the patient during the medical procedure. When the medical procedure is completed, the surgery swappable wearable device can communicate the sync data to the first synchronization platform. The first synchronization platform can then communicate the sync data to the second synchronization platform. The patient can then be moved to the recovery room and receive a recovery swappable wearable device and the second swappable wearable device can receive the sync data from the first synchronization platform.

One advantage of the second computing device receiving, at a second location, the sync data from the first computing device at a first location is that the sync data can be accessed from a plurality of different locations. For example, the first computing device can be a base station and the second computing device can be a remote station or relay station configured to that transfer sync data between a swappable wearable device and the base station. In another example, if a user forgets a swappable wearable device (such as while on vacation or traveling) the user can replace the swappable wearable device. In this example, a relay station can be configured to receive sync data of the forgotten swappable wearable device from the base station where the sync data of the forgotten swappable wearable device is stored and the relay station can communicate the sync data of the forgotten swappable wearable device to a replacement swappable wearable device. The synchronization of the sync data maintains a continuity of data between the forgotten swappable wearable device and the replacement swappable wearable device. Another advantage of the second computing device receiving, at the second location, the sync data from the first computing device at a first location is that different devices can be used at different locations (such as different configurations of swappable wearable devices) and continuity of data can be maintained between the different devices at the different locations.

In one embodiment, the first location can be a medical facility, such as a hospital, and the second location can be a residence or home of a patient of the medical facility. One advantage of synchronizing sync data between the first location and second location is that a user, such as a medical patient, can use a first swappable wearable device while at the medical facility and use a second swappable wearable device while at the home of the user and the patient can be continuously monitored while at either location. For example, a patient at a hospital can use the first swappable wearable device at the hospital, turn in the first swappable wearable device into the hospital when the patient is discharged, and then use the second swappable wearable device to continue to continue to monitor the patient when the patient arrives at home from the point. In this example, the second swappable wearable device can resume monitoring the patient from the last point where the first swappable wearable device ceased monitoring the patient.

In one embodiment, the swappable wearable device and/or the synchronization platform can monitor, store, and/or track a location of: a user, the swappable wearable device, and/or a synchronization platform at different locations. In another embodiment, the swappable wearable device and/or the synchronization platform can associate sync data with a location of the user, the swappable wearable device, and/or the synchronization platform.

Figure 18:
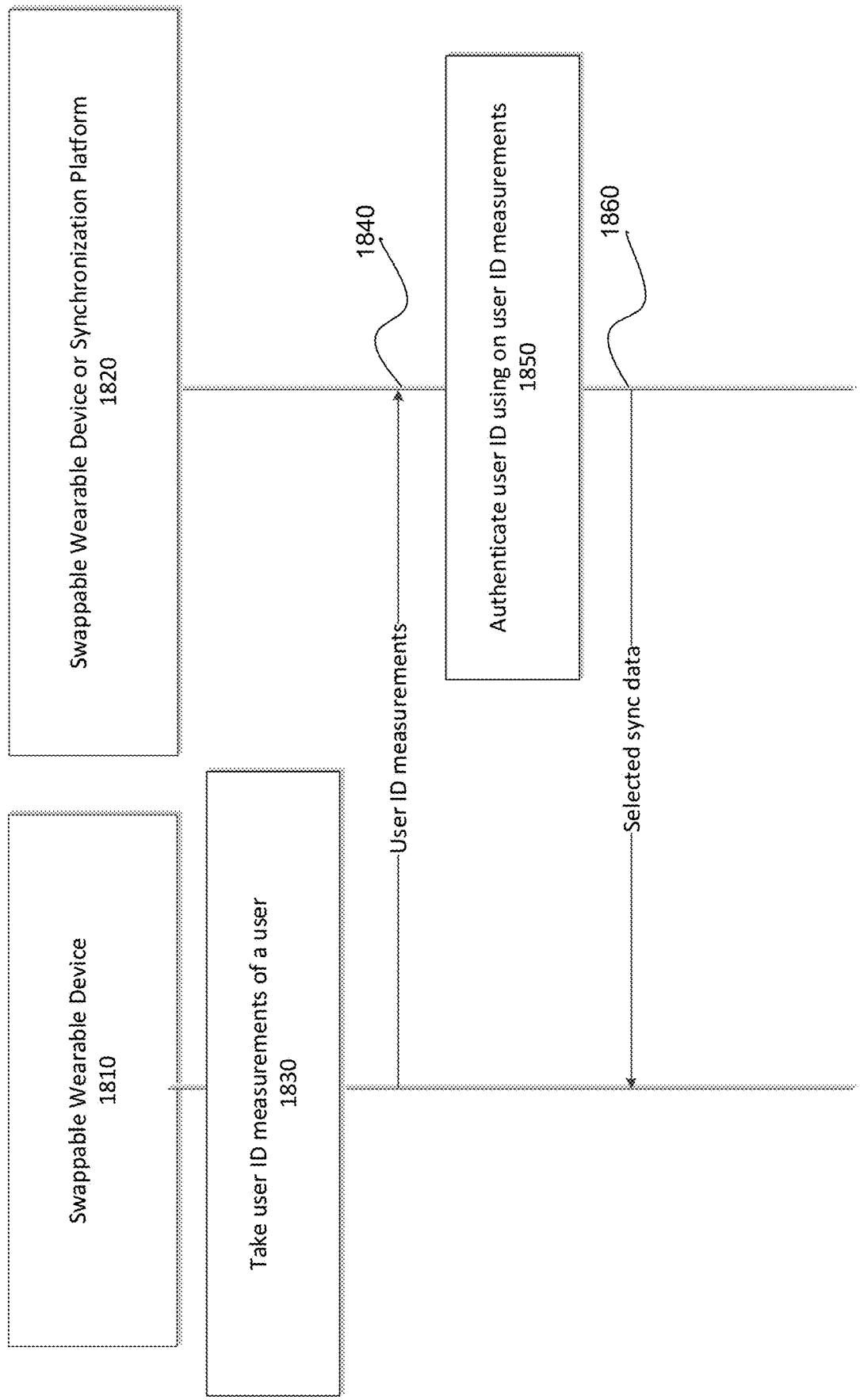
FIG. 18 depicts the functionality of circuitry of a swappable wearable device operable to authenticate a user identification (ID) in order to receive sync data in accordance with an example.

FIG. 18 uses a flow chart 1800 to illustrate the functionality of one embodiment of a swappable wearable device 1810 operable to authenticate a user identification (ID) in order to receive sync data. The functionality may be implemented as a method or the functionality may be executed as instructions on a machine, where the instructions are included on at least one computer readable medium or one non-transitory machine readable storage medium. In one example, the swappable wearable device 1810 can take user ID measurements of the user, as in block 1830. In one embodiment, the swappable wearable device can take user ID measurements of the user by taking biometric measurements of the user, such as authenticating unique biometric data of the user (for example, a resting heart rate, blood pressure, and oxygen saturation of the individual). In one example, the swappable wearable device can communicate the user ID measurements to another swappable wearable device and/or a synchronization platform 1820, as in block 1840.

In another example, the other swappable wearable device and/or the synchronization platform 1820 can be configured to authenticate the user ID of the user using, at least in part, one or more user ID measurements, as in block 1850. In another example, the other swappable wearable device and/or the synchronization platform 1820 can communicate selected sync data to the swappable wearable device 1810 when the user ID of the user has been authenticated, as in block 1860. In another example, the user can be a medical patient and the sync data can include a patient ID of the medical patient, medical records of the medical patient, medical measurement information of the medical patient, vital sign information of the medical patient, and so forth. In another embodiment, the swappable wearable device 1810 can communicate a device ID and/or an authentication ID to the other swappable wearable device and/or the synchronization platform 1820. In this embodiment, the other swappable wearable device and/or the synchronization platform 1820 can authenticate the device ID or an authentication ID before sending the selected sync data to the swappable wearable device 1810.

In one embodiment, sync data for a plurality of users and/or swappable wearable devices can be communicated and/or stored on the other swappable wearable device and/or the synchronization platform 1820. When the other swappable wearable device and/or the synchronization platform 1820 authenticates the biometric ID, the user ID, the authentication ID, and/or the device ID, the swappable wearable device 1810 can access sync data for one or more of the plurality of users.

In one embodiment, a swappable wearable device can determine a biometric ID of a user, a user ID, an authentication ID, and/or a device ID and associate selected sync data with the biometric ID of the user, the user ID, and/or the device ID.

Figure 19:
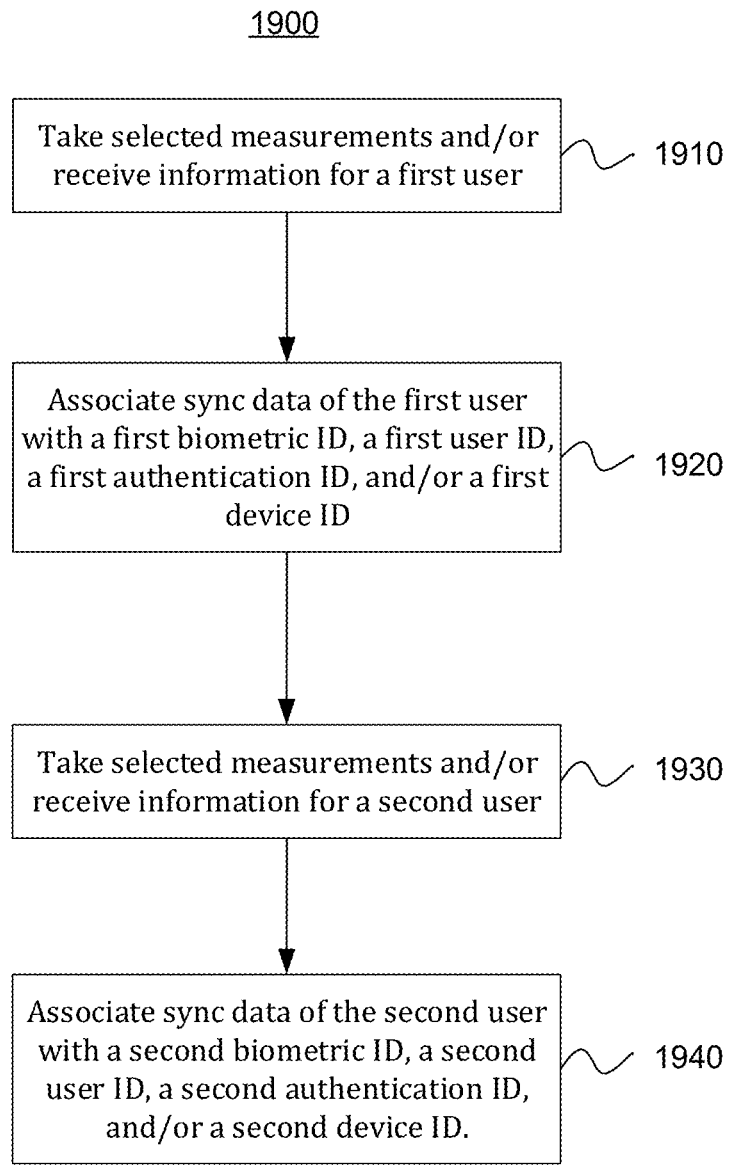
FIG. 19 depicts the functionality of a swappable wearable device or a synchronization platform operable to associate sync data with a user, a user ID, an authentication ID, and/or a device ID and associate selected sync data with the biometric ID of the user, the user ID, and/or the device ID in accordance with an example.

FIG. 19 uses a flow chart 1900 to illustrate the functionality of one embodiment of a swappable wearable device or a synchronization platform operable to associate sync data with a user, a user ID, an authentication ID, and/or a device ID and associate selected sync data with the biometric ID of the user, the user ID, and/or the device ID. The functionality may be implemented as a method or the functionality may be executed as instructions on a machine, where the instructions are included on at least one computer readable medium or one non-transitory machine readable storage medium. In one example, the swappable wearable device or the synchronization platform can take selected measurements and/or receive information for a first user, as in block 1910. In another example, the swappable wearable device or the synchronization platform can be configured to associate sync data of the first user with a first biometric ID, a first user ID, a first authentication ID, and/or a first device ID, as in block 1920. In another example, a second user can then use the swappable wearable device or the synchronization platform and the swappable wearable device or the synchronization platform can take selected measurements and/or receive information for a second user, as in block 1930. In another example, the swappable wearable device or the synchronization platform can associate sync data of the second user with a second biometric ID, a second user ID, a second authentication ID, and/or a second device ID, as in block 1940. One advantage of associating sync data of users with different a biometric ID, a user ID, and/or a device ID of the user can be to enable multiple users to use the same swappable wearable device and maintain separate sync data for each of the users.

In another embodiment, a first swappable wearable device or a first synchronization platform can communicate sync data, such as medical data or medical patient information, to a second swappable wearable device or a second synchronization platform via a server or cloud storage device (such as a cloud storage server). One advantage of communicating the sync data via the server or cloud storage device is to maintain security of the sync data, such as to comply with Health Insurance Portability and Accountability Act (HIPAA) requirements of the United States department of health and human services. For example, the sync data can be collected and aggregated from one or more swappable wearable devices and/or one or more synchronization platform at a single device, such as a server, and then communicated from a single device to a medical facility device (such as a hospital server) in a format and/or procedure compliant with HIPAA standards data. In one embodiment, communicating the aggregated sync data from the server or the cloud storage device can minimize a security breach of information from different of swappable wearable devices and/or synchronization platforms. In another embodiment, communicating the aggregated sync data from the server or cloud storage device can enable a single device to communicate HIPAA compliant data and reduce or eliminate each swappable wearable device and/or synchronization platform from being required to individually format the sync data to a HIPAA compliant data standard or format.

Figure 20:
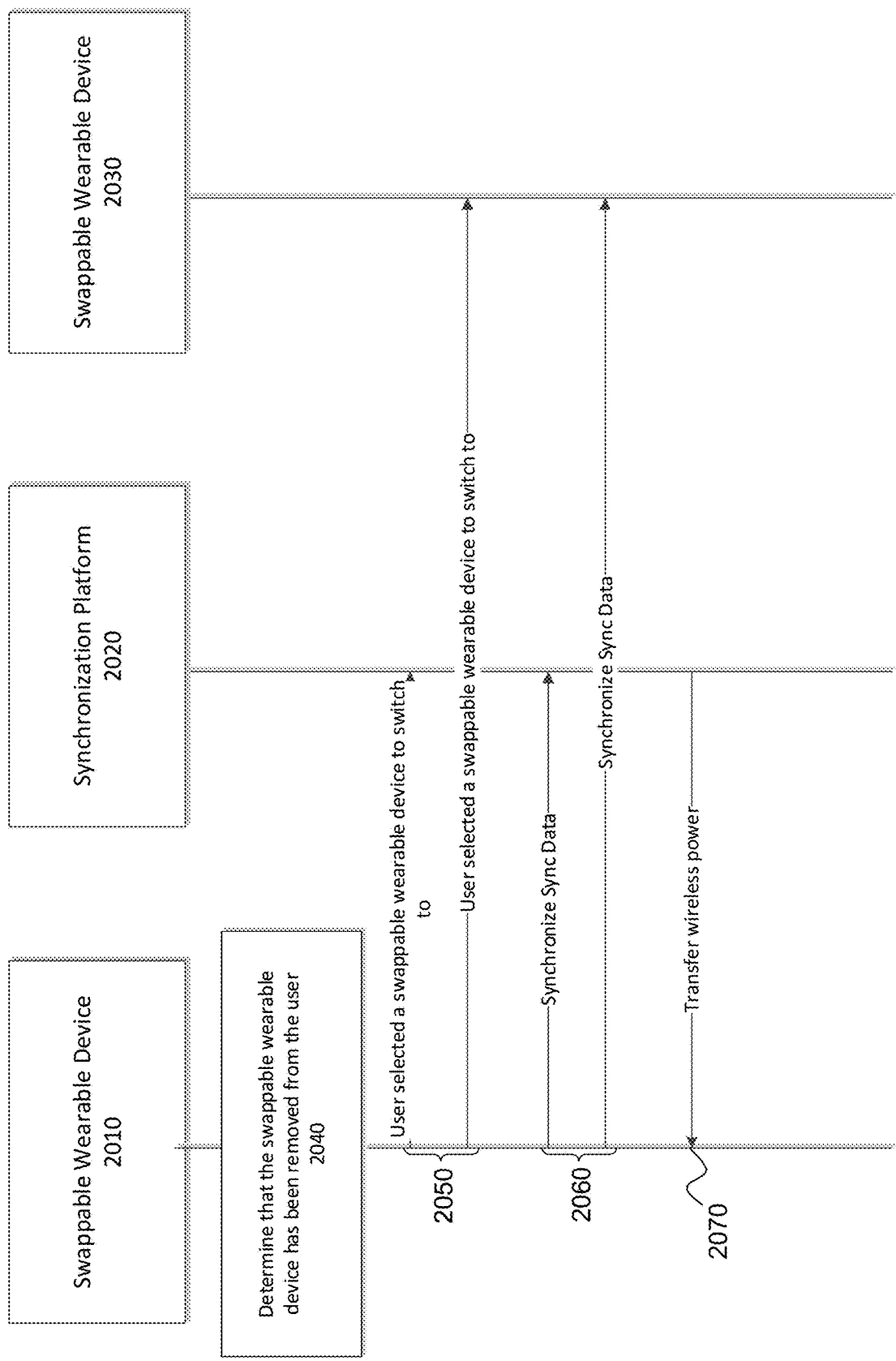
FIG. 20 depicts the functionality of a synchronization platform operable to provide power, such as wireless power, and/or synchronize sync data to a plurality of swappable wearable devices and coupled to the synchronization platform in accordance with an example.

FIG. 20 illustrates a synchronization platform 2020 operable to provide power, such as wireless power, and/or synchronize sync data to a plurality of swappable wearable devices 2010 and 2030 coupled to the synchronization platform 2020. In one example, a user of a swappable wearable device 2010 can select another swappable wearable device 2030 to switch with the swappable wearable device 2010. In one example, the swappable wearable device 2010 can be configured to determine that the swappable wearable device 2010 has been removed from the user, as in block 2040. In one embodiment, the synchronization platform 2020 and/or the other swappable wearable device 2030 can determine when the other swappable wearable device 2030 that has been selected by the user by determining when the user has removed the other swappable wearable device 2030 from the synchronization platform 2020. In another example, when the swappable wearable device 2010 has determined that the user has removed the swappable wearable device 2010, the swappable wearable device 2010 can be configured to communicate to the synchronization platform 2020 and/or the other swappable wearable device 2030 that the user has selected one or more of the plurality of swappable wearable devices 2030 to switch with the swappable wearable device 2010, as in block 2050.

In one configuration, the swappable wearable device 2010 can communicate to the synchronization platform 2020 and/or the plurality of swappable wearable devices 2030 using a communications network, such as a wireless network or a cellular network. In another example, when the user has selected the other swappable wearable device 2030 to for use, the swappable wearable device 2010 can synchronize sync data with the synchronization platform 2020 and/or the other swappable wearable device 2030, as in block 2060. In another example, when the user has selected the other swappable wearable device 2030 to for use, the synchronization platform 2020 can transfer wireless power to the swappable wearable device 2010, as in block 2070. In one embodiment, the other swappable wearable device 2030 can be a plurality of other swappable wearable devices.

In one embodiment, the synchronization platform 2020 can provide power and/or synchronize information with a plurality of different types of swappable wearable devices. In one example, a user can use a swappable wristband device while awake during the day and use a swappable ankle band device while the user sleeps during the night. In another example, a user can use a swappable headband device while exercising and use a swappable wristband device during normal daily activities. In this example, the synchronization platform can provide power to a currently unused device, such as the swappable headband device, and synchronize information from the swappable wristband device to the swappable headband device when a user switches from normal daily activities to exercise activities and recharge the swappable wristband device during the period of the exercise activities.

One advantage of the other swappable wearable device 2030 synchronizing with the swappable wearable device 2010 is that when a user (such as a medical patient at a hospital or a member of a sports team) that desires to switch the swappable wearable device 2010 with the other swappable wearable device 2030 (such as when a battery of the swappable wearable device 2010 is dead or the swappable wearable device 2010 is malfunctioning) the user can select one or more other swappable wearable devices 2030 and the sync data will be synchronized automatically to the selected one or more other swappable wearable devices 2030.

Figure 21:
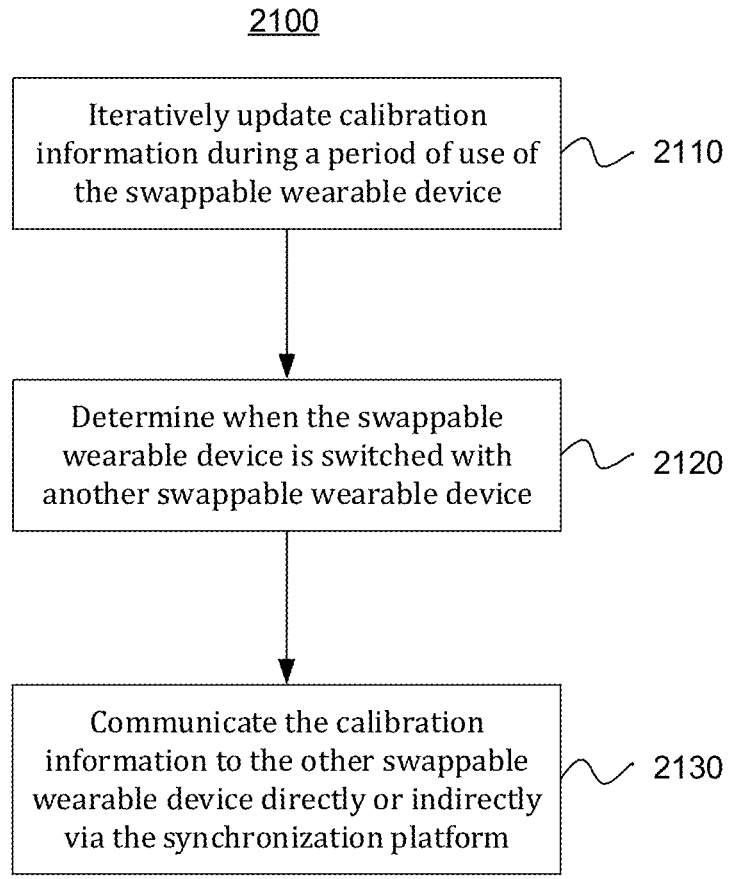
FIG. 21 depicts the functionality of a swappable wearable device operable to communicate synchronization information to another swappable wearable device in accordance with an example.

FIG. 21 uses a flow chart 2100 to illustrate the functionality of one embodiment of the circuitry of a swappable wearable device operable to communicate synchronization information to another swappable wearable device. The functionality may be implemented as a method or the functionality may be executed as instructions on a machine, where the instructions are included on at least one computer readable medium or one non-transitory machine readable storage medium. In one embodiment, the circuitry can be configured to iteratively update calibration information during a period of use of the swappable wearable device, as in block 2110. In another embodiment, the circuitry can be configured to determine when the swappable wearable device is switched with another swappable wearable device, as in block 2120. In another embodiment, the circuitry can be configured to communicate the calibration information to the other swappable wearable device directly or indirectly via the synchronization platform, as in block 2130.

Figure 22:
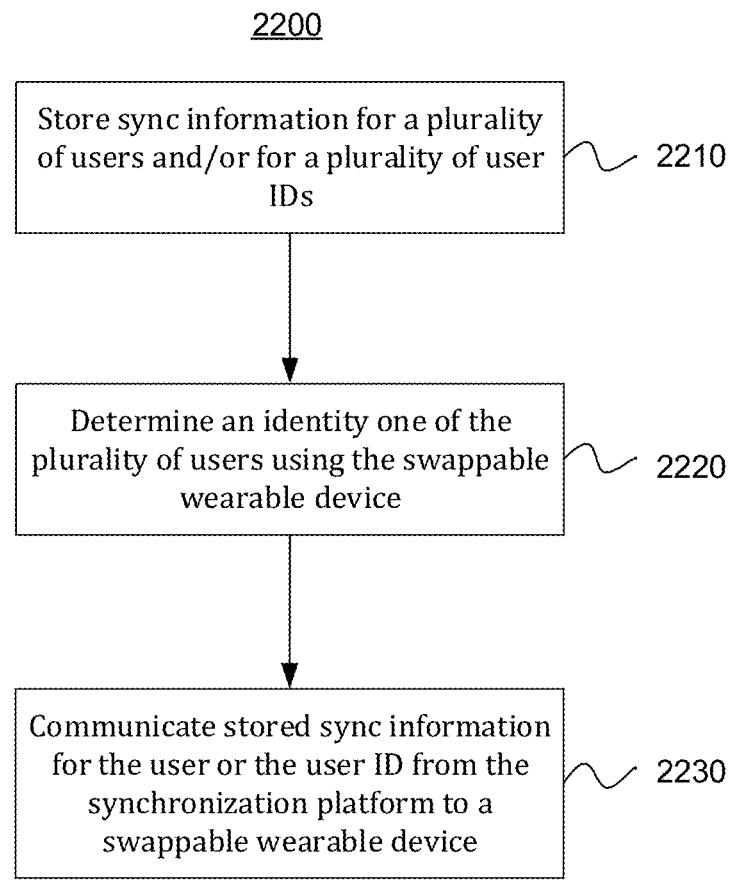
FIG. 22 depicts the functionality of a circuitry of a synchronization platform operable to communicate sync data to a swappable wearable device for different users in accordance with an example.

FIG. 22 uses a flow chart 2200 to illustrate the functionality of one embodiment of the circuitry of a synchronization platform operable to communicate sync data to a swappable wearable device for different users. The functionality may be implemented as a method or the functionality may be executed as instructions on a machine, where the instructions are included on at least one computer readable medium or one non-transitory machine readable storage medium. In one embodiment, the circuitry can be configured to store sync information for a plurality of users and/or for a plurality of user IDs, as in block 2210. In another embodiment, the circuitry can be configured to determine an identity one of the plurality of users using the swappable wearable device, as in block 2220. In another embodiment, when the synchronization platform has determined the identity of the individual using the swappable wearable device, the circuitry can be configured to communicate stored sync information for the user or the user ID from the synchronization platform to a swappable wearable device, as in block 2230.

Figure 23:
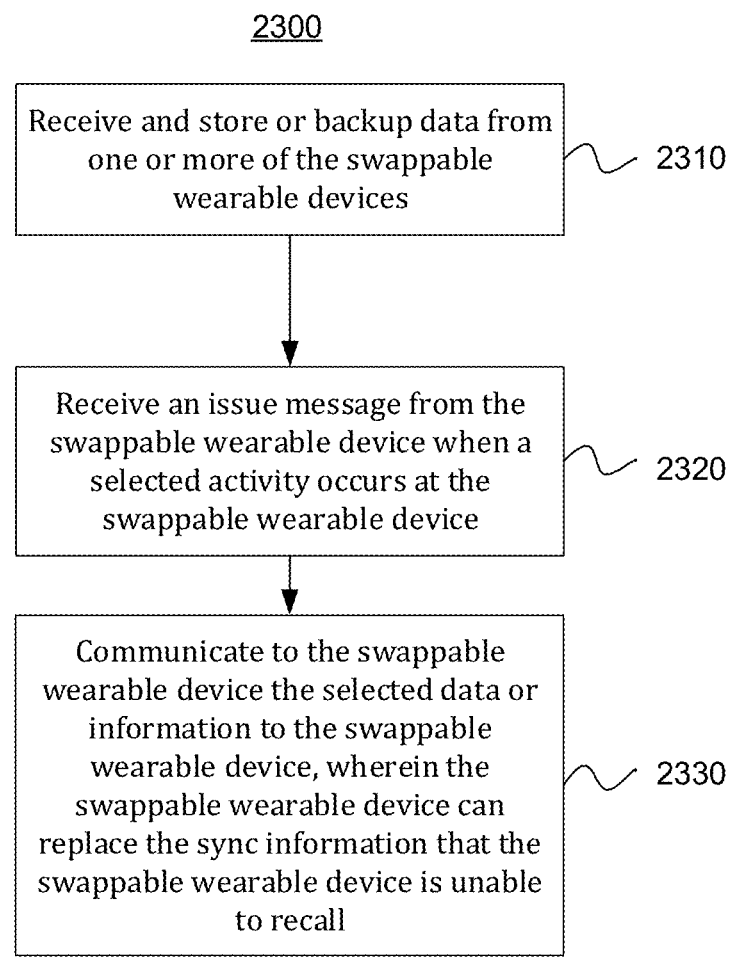
FIG. 23 depicts the functionality of a synchronization platform operable to backup data for one or more swappable wearable devices in accordance with an example.

FIG. 23 uses a flow chart 2300 to illustrate the functionality of one embodiment of the circuitry of a synchronization platform operable to backup data (such as sync data) for one or more swappable wearable devices. The functionality may be implemented as a method or the functionality may be executed as instructions on a machine, where the instructions are included on at least one computer readable medium or one non-transitory machine readable storage medium. In one embodiment, the circuitry can be configured to receive and store or backup data from one or more of the swappable wearable devices, as in block 2310. In another embodiment, the circuitry can be configured to receive an issue message from a swappable wearable device when a selected activity occurs at the swappable wearable device, as in block 2320. In one example, the selected activity can be when the swappable wearable device loses power, has corrupt data, malfunctions, or otherwise is unable to recall measurement information. In another example, the issue message can include a request from the swappable wearable device requesting selected data or information (such as selected sync data). In another embodiment, the circuitry can be configured to communicate to the swappable wearable device the selected data or information to the swappable wearable device, wherein the swappable wearable device can replace the sync information that the swappable wearable device is unable to recall, as in block 2330. In another embodiment, the synchronization platform can be a relay node configured to relay information from one swappable wearable device to another swappable wearable device to back up the data or information on the other swappable wearable device.

In one embodiment, the swappable wearable device and/or the synchronization platform can indicate to the user of the swappable wearable device that a power level of the swappable wearable device is below a selected threshold value. In another embodiment, when the power level of the swappable wearable device is below the selected threshold value, the swappable wearable device and/or the synchronization platform can indicate to the user to switch the swappable wearable device the user is currently using with another swappable wearable device.

In one configuration, the swappable wearable device and/or the synchronization platform can be configured to communicate with other devices, such as other devices taking medical measurements. In another configuration, the swappable wearable device and/or the synchronization platform can be configured to communicate information between the other devices and the swappable wearable device and/or the synchronization platform.

Figure 24:
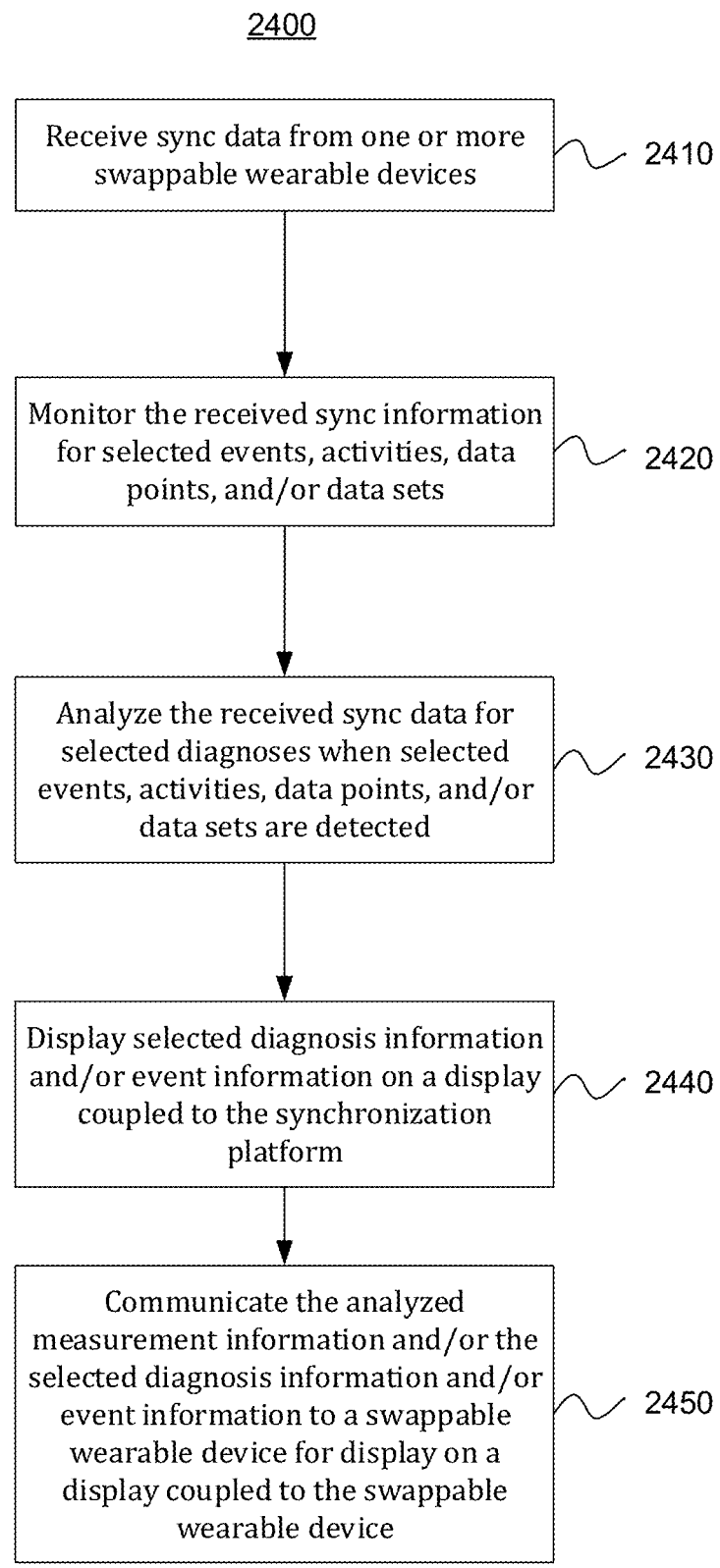
FIG. 24 depicts the functionality of a circuitry of a synchronization platform operable to analyze sync information received from one or more swappable wearable devices to determine selected measurement information or user diagnosis in accordance with an example.

FIG. 24 uses a flow chart 2400 to illustrate the functionality of one embodiment of the circuitry of a synchronization platform operable to analyze sync information received from one or more swappable wearable devices to determine selected measurement information or user diagnosis. The functionality may be implemented as a method or the functionality may be executed as instructions on a machine, where the instructions are included on at least one computer readable medium or one non-transitory machine readable storage medium. In one embodiment, the circuitry can be configured to receive sync data from one or more swappable wearable devices, as in block 2410. In another embodiment, the circuitry can be configured to monitor the received sync data for selected events, activities, data points, and/or data sets, as in block 2420. In another embodiment, the circuitry can be configured to analyze the received sync data for selected diagnosis when selected events, activities, data points, and/or data sets are detected, as in block 2430. In another embodiment, the circuitry can be configured to display selected diagnosis information and/or event information on a display coupled to the synchronization platform, as in block 2440. In one embodiment, the select diagnosis information and/or event information can include: the sync information, results of the analyzed measurement information, selected measurement information, user diagnosis information, event information, activity information, data point information, and/or data set information. In another embodiment, the circuitry can be configured to communicate the analyzed measurement information and/or the selected diagnosis information and/or event information to a swappable wearable device for display on a display coupled to the swappable wearable device, as in block 2450.

In one example, the swappable wearable device can analyze measurement information received from one or more other swappable wearable devices. In another embodiment, the swappable wearable device and/or the synchronization platform can aggregate measurement information from the swappable wearable device and/or other swappable wearable device or the synchronization platform. In another embodiment, the swappable wearable device and/or the synchronization platform can analyze the aggregated measurement information. In another embodiment, the synchronization platform can display the results of the analyzed measurement information.

In one embodiment, the synchronization platform and/or the swappable wearable device can receive medical records of the user and adjust one or more measurements and/or procedures for analyzing selected sync information based on the medical records. For example, the synchronization platform and/or the swappable wearable device can receive medical records of the user indicating the user has diabetes and adjust one or more measurements and/or procedures for analyzing based on the user having diabetes. In another embodiment, the synchronization platform can receive sync information from one or more swappable wearable devices and aggregate the received sync information with the medical records. In another embodiment, the synchronization platform can communicate the aggregated sync information to another device, such as a server at a medical facility.

Figure 25:
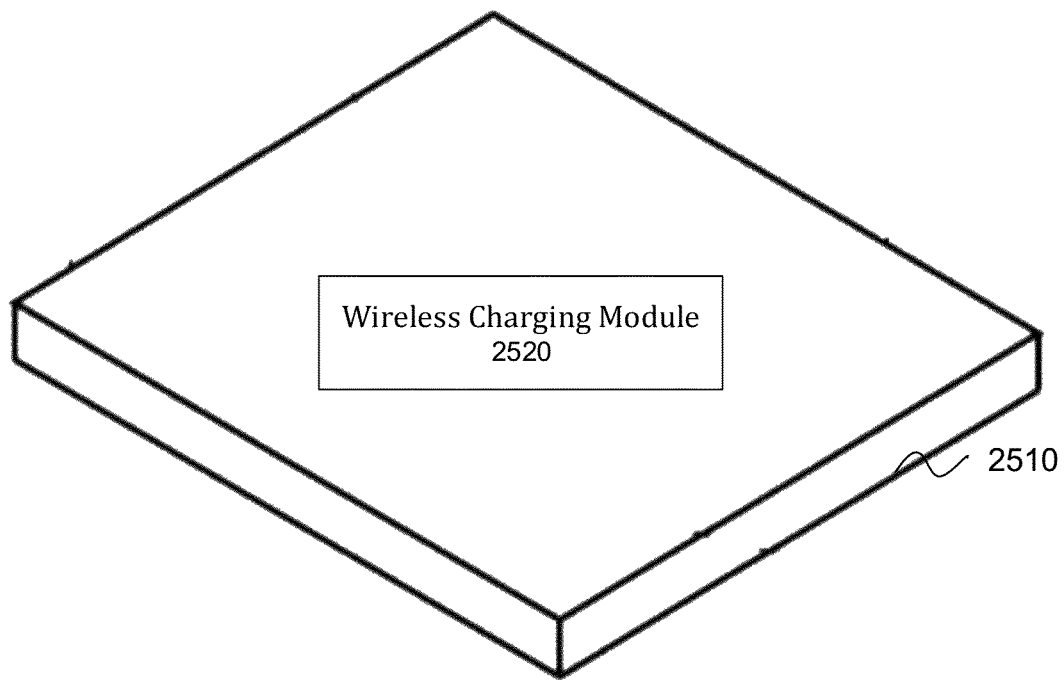
FIG. 25 shows a synchronization platform that includes a wireless charging module in accordance with an example.

FIG. 25 depicts a synchronization platform 2510 that includes a wireless charging module 2520. In one embodiment, the wireless charging module 2520 can include an induction charging coils and/or resonant charging coils. In one embodiment, when a swappable wearable device is within a threshold range of the synchronization platform 2510, the synchronization platform 2510 can use the wireless charging module 2520 to transfer energy to the swappable wearable device. In another embodiment, when a swappable wearable device is within a threshold range of the synchronization platform 2510, the synchronization platform 2510 can use the wireless charging module 2520 to communicate a data or information to the swappable wearable device. In another embodiment when a swappable wearable device is within a threshold range of the synchronization platform 2510, the synchronization platform 2510 can use the wireless charging module 2520 to communicate security information or encryption information to the swappable wearable device using the induction charging coils and/or resonant charging coils. In one example, the swappable wearable device can use the security information or encryption information to access the synchronization platform to communicate information and/or receive wireless power.

Figure 26:
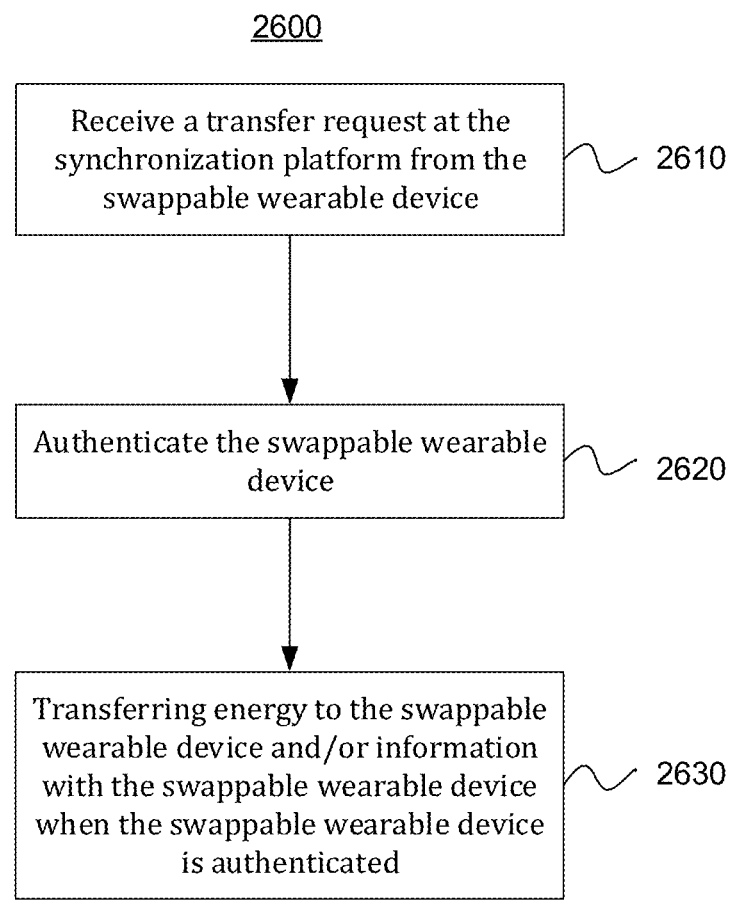
FIG. 26 depicts the functionality of a circuitry of a synchronization platform operable to authenticate a swappable wearable device before providing wireless power to the swappable wearable device and/or communicating data with the swappable wearable device in accordance with an example.

FIG. 26 uses a flow chart 2600 to illustrate the functionality of one embodiment of the circuitry of a synchronization platform operable to authenticate a swappable wearable device before providing wireless power to the swappable wearable device and/or communicating data with the swappable wearable device. The functionality may be implemented as a method or the functionality may be executed as instructions on a machine, where the instructions are included on at least one computer readable medium or one non-transitory machine readable storage medium. In one example, one or more swappable wearable devices can have a device identification (ID). In one embodiment, the circuitry can be configured to receive a transfer request at the synchronization platform from the swappable wearable device, as in block 2610. In one example, transfer request can include the device ID of the swappable wearable device. In another embodiment, the circuitry can be configured to authenticate the swappable wearable device, as in block 2620. In another embodiment, the circuitry can be configured to transferring energy to the swappable wearable device and/or information with the swappable wearable device when the swappable wearable device is authenticated, as in block 2630.

One advantage of a swappable wearable device is to reduce false alarms for false positives due to a gap in measurement data. In one example, traditionally a when a wearable device is removed from an individual to be recharged, there is a gap in the measurement data during the recharge period, such as for several hours while an individual sleeps. In this example, during the time period of the gap in measurement data, the physiology of the individual can change. In one embodiment, the physiology of the individual can change between a time when an individual removes the swappable wearable device when going to bed and reattaching the swappable wearable device when the individual wakes up the following day. In another embodiment, a first swappable wearable device can continuously monitor an individual while they are awake and then be recharged while the individual sleeps while a second swappable wearable device recharges while the individual is awake and monitors the individual while the individual is sleep, thereby reducing and/or substantially eliminating the gap in measurement information. One advantage of reducing and/or eliminating the gap in measurement information is to eliminate a false positive due to a change in the physiology of the individual during a recharging period.

Figure 27:
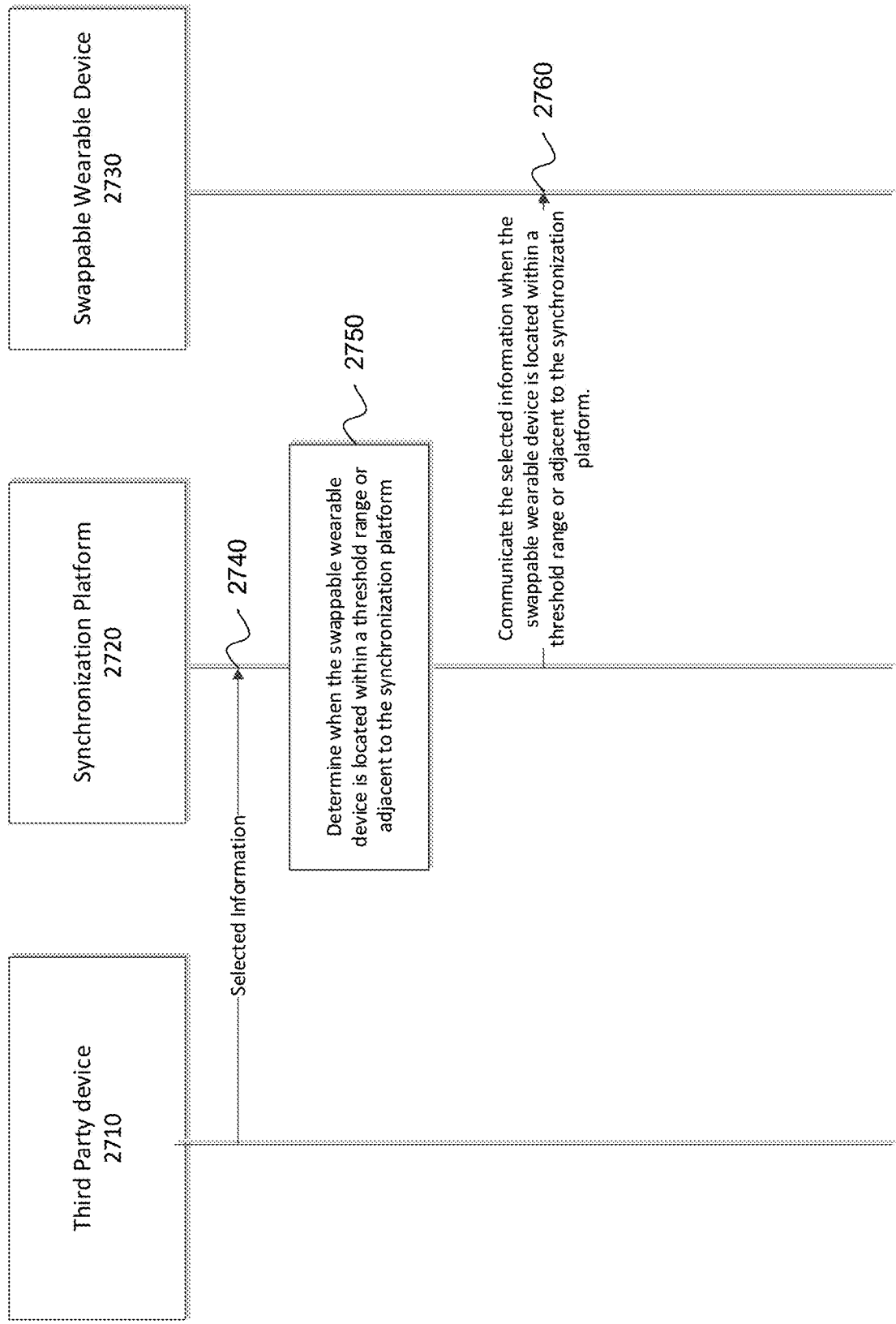
FIG. 27 depicts the functionality of a circuitry of a swappable wearable device operable to receive information from a third party device using a synchronization platform in accordance with an example.

FIG. 27 uses a flow chart 2700 to illustrate the functionality of one embodiment of the circuitry of a swappable wearable device 2730 operable to receive information from a third party device 2710, such as a medical professional, using a synchronization platform 2720. The functionality may be implemented as a method or the functionality may be executed as instructions on a machine, where the instructions are included on at least one computer readable medium or one non-transitory machine readable storage medium. In one example, the third party device 2710 (such as a server) can communicate selected information, such as medical information, to the synchronization platform 2720, as in block 2740. In another example, the synchronization platform 2720 can determine when the swappable wearable device 2730 is located within a threshold range or adjacent to the synchronization platform 2720, as in block 2750. In another example, when the swappable wearable device 2730 is located within a threshold range or adjacent to the synchronization platform 2720, the synchronization platform 2720 can communicate the selected information to the swappable wearable device 2730, as in block 2760. In one embodiment, an individual can use a first swappable wearable device to take measurement information and the synchronization platform can aggregate the measurement information of the first swappable wearable device with the received medical information received from a third party device. In this embodiment, the synchronization platform can the aggregated information to a second swappable wearable device to provide the second swappable wearable device with updated information when the individual swaps the first swappable wearable device with the second swappable wearable device.

In one embodiment, communication between the synchronization platform and one or more swappable wearable devices can be a closed communicate loop. In one example, the swappable wearable device can only communicate sync information with the synchronization platform and/or other swappable wearable devices. In another embodiment, the closed communicate loop can include the synchronization platform communicating information with another selected device, such as a server or other device. In another embodiment, the synchronization platform can be a communications hub for information from swappable wearable devices and other devices.

Figure 28:
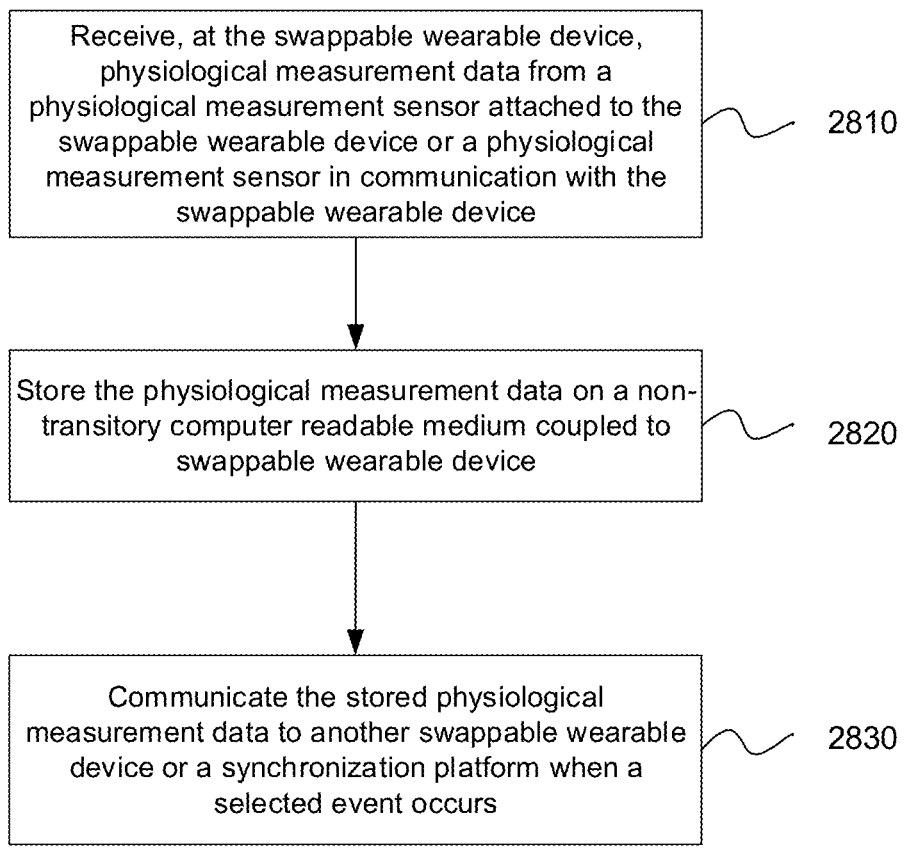
FIG. 28 depicts the functionality of a circuitry of a swappable wearable device operable to monitor physiological parameters of a user in accordance with an example.

Another example provides functionality 2800 of circuitry of a swappable wearable device operable to monitor physiological parameters of a user, as shown in the flow chart in FIG. 28. The functionality may be implemented as a method or the functionality may be executed as instructions on a machine, where the instructions are included on at least one computer readable medium or one non-transitory machine readable storage medium. The circuitry can be configured to receive, at the swappable wearable device, physiological measurement data from a physiological measurement sensor attached to the swappable wearable device or a physiological measurement sensor in communication with the swappable wearable device, as in block 2810. The circuitry can be further configured to store the physiological measurement data on a non-transitory computer readable medium coupled to swappable wearable device, as in block 2820. The circuitry can be further configured to communicate the stored physiological measurement data to another swappable wearable device or a synchronization platform when a selected event occurs, as in block 2830.

In one embodiment, the selected event includes: receiving a data transfer request from the other swappable wearable device or the synchronization platform; a selected time of day is arrived at; a selected activity occurs; or the swappable wearable device is within a selected distance of the other swappable wearable device or the synchronization platform. In another embodiment, the circuitry can be further configured to determine when the swappable wearable device has been removed from a user and communicate the stored physiological measurement data to the other swappable wearable device or the synchronization platform. In another embodiment, the circuitry can be further configured to receive wireless power from the synchronization platform using a wireless transfer coil.

In one example, the circuitry can be further configured to analyze the received physiological measurement data or the stored physiological measurement data to determine a selected physiological condition of the user of the swappable wearable device. In another example, the circuitry can be further configured to communicate selected data with another swappable wearable device or a computing device. In another example, the circuitry can be further configured to communicate backup information to the other swappable wearable device or the synchronization platform when a selected event occurs.

Figure 29:
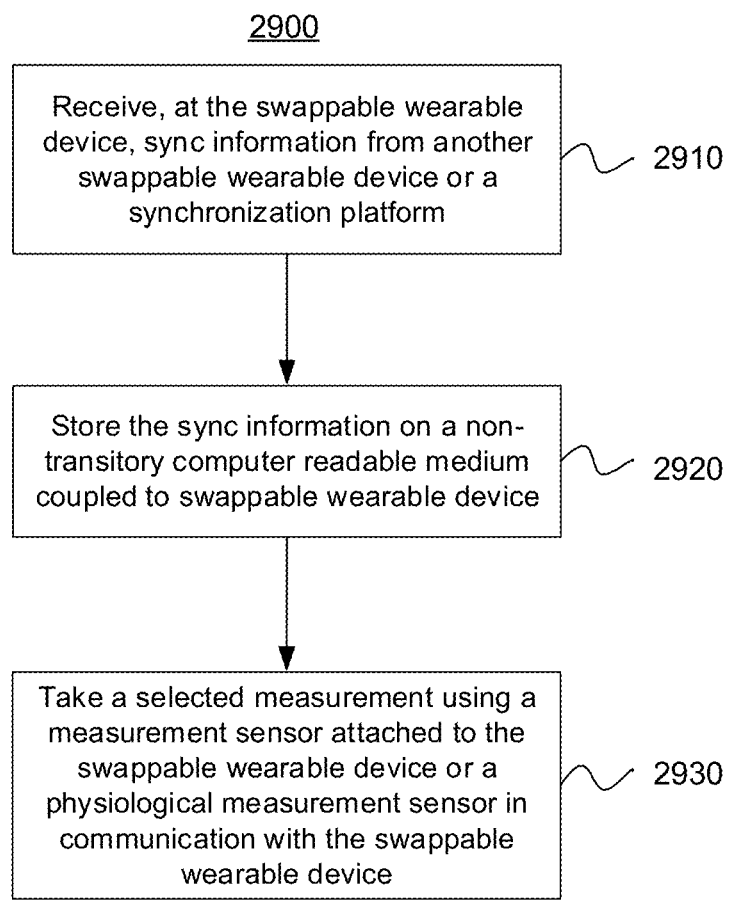
FIG. 29 depicts the functionality of a circuitry of a swappable wearable device operable to take selected measurements of a user in accordance with an example.

Another example provides functionality 2900 of circuitry of a swappable wearable device operable to take selected measurements of a user, as shown in the flow chart in FIG. 29. The functionality may be implemented as a method or the functionality may be executed as instructions on a machine, where the instructions are included on at least one computer readable medium or one non-transitory machine readable storage medium. The circuitry can be configured to receive, at the swappable wearable device, sync information from another swappable wearable device or a synchronization platform, as in block 2910. The circuitry can be further configured to store the sync information on a non-transitory computer readable medium coupled to swappable wearable device, as in block 2920. The circuitry can be further configured to take a selected measurement using a measurement sensor attached to the swappable wearable device or a physiological measurement sensor in communication with the swappable wearable device, as in block 2930.

In one embodiment, the circuitry can be further configured to normalize at least a selected portion of sync information with the physiological measurement data. In another embodiment, the circuitry can be further configured to: communicate, to the synchronization platform, selected measurement information taken using the measurement sensor; receive, from the synchronization platform, normalization information; and adjust the selected measurement information using the normalization information. In another embodiment, the circuitry can be further configured to align selected sync information received from the other swappable wearable device, wherein the selected sync information from the other swappable wearable device includes measurement information from a measurement sensor attached to the other swappable wearable device or a physiological measurement sensor in communication with the other swappable wearable device.

In one example, the circuitry can be further configured to receive wireless power from the synchronization platform. In another example, the circuitry can be further configured to calibrate the measurement sensor attached to the swappable wearable device or the physiological measurement sensor in communication with the swappable wearable device using the received sync information. In another example, the circuitry can be further configured to communicate sync information with other wearable devices or non-wearable devices.

Figure 30:
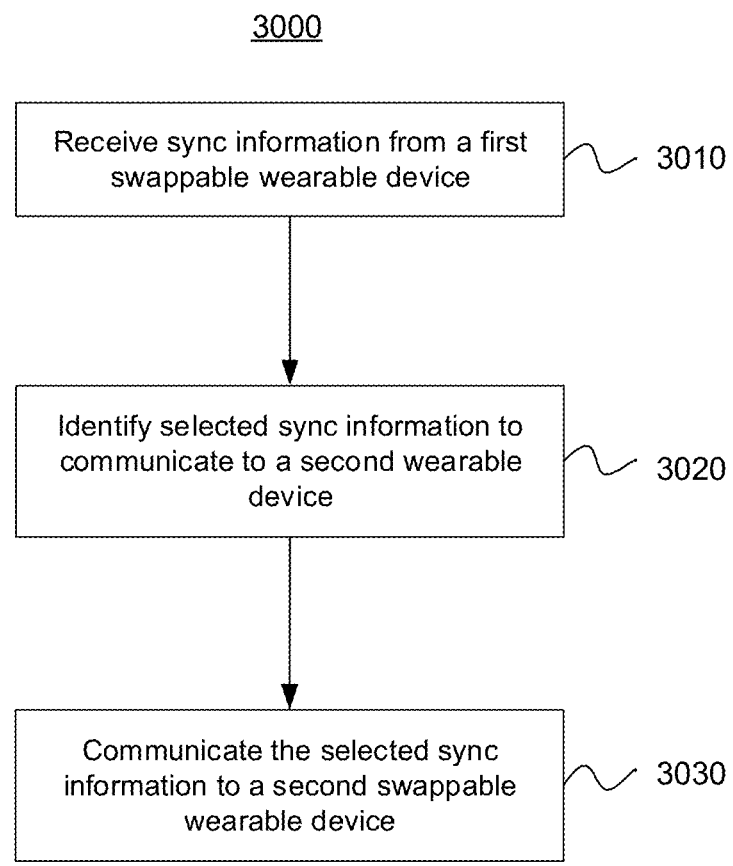
FIG. 30 depicts the functionality of a circuitry of a synchronization platform operable to communicate sync information to a computing device in accordance with an example.

Another example provides functionality 3000 of circuitry of a synchronization platform operable to communicate sync information to a computing device, as shown in the flow chart in FIG. 30. The functionality may be implemented as a method or the functionality may be executed as instructions on a machine, where the instructions are included on at least one computer readable medium or one non-transitory machine readable storage medium. The circuitry can be configured to receive sync information from a first swappable wearable device, as in block 3010. The circuitry can be further configured to identify selected sync information to communicate to a second wearable device, as in block 3020.

The circuitry can be further configured to communicate the selected sync information to a second swappable wearable device, as in block 3030.

In one embodiment, the circuitry can be further configured to verify the information communicated to the second swappable wearable device is the same as the information received from the first swappable wearable device. In another embodiment, the circuitry can be further configured to establish a communication link between the first swappable wearable device and the second swappable wearable device. In another embodiment, the circuitry can be further configured to establish a communication link with the first swappable wearable device or the second swappable wearable device. In another embodiment, the circuitry can be further configured to receive sync information from the second swappable wearable device and normalize the sync information from the first swappable wearable device with the sync information from the second swappable wearable device.

In one example, the circuitry can be further configured to detect when the first swappable wearable device or the second swappable wearable device is within a threshold distance and establish a communication link with the first swappable wearable device or the second swappable wearable device when the first swappable wearable device or the second swappable wearable device within the threshold distance. In another example, the circuitry can be further configured to provide wireless power to the first swappable wearable device or the second swappable wearable device. In another example, the circuitry can be further configured to communicate firmware updates, software update, or operating system updates to the first swappable wearable device or the second swappable wearable device. In another example, the circuitry can be further configured to receive selected medical information from another device and communicate the selected medical information to the first swappable wearable device or the second swappable wearable device. In another example, the circuitry can be further configured to analyze the sync information from the first swappable wearable device to determine a selected medical diagnosis or receive sync information from the second swappable wearable device and analyze the received sync information from the second swappable wearable device to determine a selected medical diagnosis.

Figure 31:
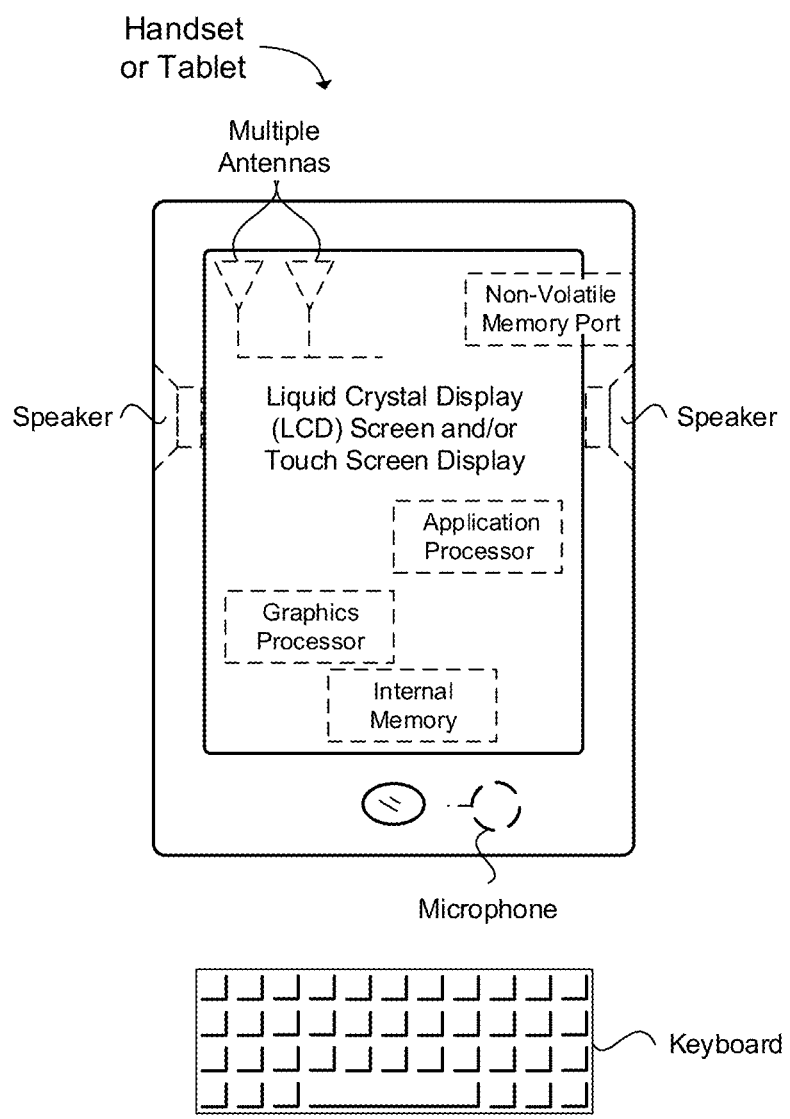
FIG. 31 illustrates a diagram of a device in accordance with an example.

FIG. 31 provides an example illustration of the device, such as a user equipment (UE), a synchronization platform, a swappable wearable device, a mobile wireless device, a mobile communication device, a tablet, a handset, or other type of wireless device. The device can include one or more antennas configured to communicate with a node or transmission station, such as a base station (BS), an evolved Node B (eNode B), a baseband unit (BBU), a remote radio head (RRH), a remote radio equipment (RRE), a relay station (RS), a radio equipment (RE), a remote radio unit (RRU), a central processing module (CPM), or other type of wireless wide area network (WWAN) access point. The device can be configured to communicate using at least one wireless communication standard including 3GPP LTE, WiMAX, High Speed Packet Access (HSPA), Bluetooth, and Wi-Fi. The device can communicate using separate antennas for each wireless communication standard or shared antennas for multiple wireless communication standards. The device can communicate in a wireless local area network (WLAN), a wireless personal area network (WPAN), and/or a WWAN.

FIG. 31 also provides an illustration of a microphone and one or more speakers that can be used for audio input and output from the device. The display screen may be a liquid crystal display (LCD) screen, or other type of display screen such as an organic light emitting diode (OLED) display. The display screen can be configured as a touch screen. The touch screen may use capacitive, resistive, or another type of touch screen technology. An application processor and a graphics processor can be coupled to internal memory to provide processing and display capabilities. A non-volatile memory port can also be used to provide data input/output options to a user. The non-volatile memory port may also be used to expand the memory capabilities of the wireless device. A keyboard may be integrated with the wireless device or wirelessly connected to the wireless device to provide additional user input. A virtual keyboard may also be provided using the touch screen.

Various techniques, or certain aspects or portions thereof, may take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, EPROM, flash drive, optical drive, magnetic hard drive, or other medium for storing electronic data. The base station and mobile station may also include a transceiver module, a counter module, a processing module, and/or a clock module or timer module. One or more programs that may implement or utilize the various techniques described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Reference throughout this specification to "an example" means that a particular feature, structure, or characteristic described in connection with the example is included in at least one embodiment of the present invention. Thus, appearances of the phrases "in an example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as defacto equivalents of one another, but are to be considered as separate and autonomous representations of the present invention.

Furthermore, the described features, structures, or characteristics may be combined in any suitable manner in one or more embodiments. In the foregoing description, numerous specific details are provided, such as examples of layouts, distances, network examples, etc., to provide a thorough understanding of embodiments of the invention. One skilled in the relevant art will recognize, however, that the invention can be practiced without one or more of the specific details, or with other methods, components, layouts, etc. In other instances, well-known structures, materials, or operations are not shown or described in detail to avoid obscuring aspects of the invention.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed:

1. A calibration platform having circuitry configured to:
    establish a first communication link with a first swappable wearable device being worn on a body of a user;
    receive a first set of measurement data from a first sensor of the first swappable wearable device indicative of physiological measurements of the user and the first set of measurement data corresponds to a first location on the body of the user, wherein the first sensor is located proximate a first location of the user and the first set of measurement data corresponds to the first location of the user;
    receive a second set of measurement data from the first sensor;
    determine that the second set of measurement data from a first sensor of the first swappable wearable device indicates that the first swappable wearable device is not engaged with the body;
    in response to the first swappable wearable device being removed from the body
        receive power information indicating when the first swappable wearable device is being charged;
    in response to the first swappable wearable device being removed from the body and receiving the power information, send update data to the first swappable device;
    in response to the first swappable wearable device being removed from the body and replaced with a second swappable wearable device at the first location of the user that is a same type as the first swappable wearable device:
        establish a second communication link with the second swappable wearable device;
        receive a third set of measurement data of the first type from a second sensor of the second swappable wearable device indicative of the physiological measurements of the user;
        generate calibration information for the second swappable wearable device based on the third set of measurement data and at least one of the first set of measurement data or the second set of measurement data corresponding to the first location of the user, wherein the calibration information is configured to:
            align the third set of measurement data with the first set of measurement data or the second set of measurement data; and
            calibrate the second swappable wearable device based on the first set of measurements data taken by the first sensor at the first location of the user and the third set of measurement data taken by the second sensor at the first location of the user;
        communicate the calibration information to the second swappable wearable device to calibrate the second swappable wearable device to generate the third set of measurement data, at the first location of the user, wherein the third set of measurement data is a continuation of the first set of measurement data.

2. The calibration platform of claim 1, further configured to verify the calibration information communicated to the second swappable wearable device is based on the first set of measurement data or the second set of measurement data received from the first swappable wearable device.

3. The calibration platform of claim 1, further configured to establish a two-way communication link between the first swappable wearable device and the second swappable wearable device.

4. The calibration platform of claim 1, further configured to establish a relay communication link between the first swappable wearable device and the second swappable wearable device.

5. The calibration platform of claim 1, further configured to
    normalize the the first set of measurement data from the first swappable wearable device with the the third set of measurement data from the second swappable wearable device.

6. The calibration platform of claim 1, further configured to:
    detect when the first swappable wearable device or the second swappable wearable device is within a threshold distance of the calibration platform; and establish a communication link with the first swappable wearable device or the second swappable wearable device when the first swappable wearable device or the second swappable wearable device within the threshold distance.

7. The calibration platform of claim 1, further configured to provide wireless power to the first swappable wearable device or the second swappable wearable device.

8. The calibration platform of claim 1, wherein the update data is a firmware update, a software update, or an operating system update.

9. The calibration platform of claim 1, further configured to:
receive selected medical information from another device; and
communicate the selected medical information to the first swappable wearable device or the second swappable wearable device.

10. The calibration platform of claim 1, further configured to analyze the the first set of measurement data from the first swappable wearable device to determine a selected medical diagnosis.

11. A device, comprising:
a processing device being configured to:
establish a first communication link with a first wearable device being worn on a body of a user at a first point in time;
receive a first set of measurement data of a first type from a first sensor of the first wearable device indicative of physiological measurements from the user, wherein the first sensor is located proximate a first location of the user and the first set of measurement data corresponds to the first location of the user;
receive a second set of measurement data from the first sensor;
determine that the second set of measurement data indicates that the first wearable device is not engaged with the body; and
in response to the first wearable device being removed from the body at the first location of the user and replaced with a second wearable device at the first location of the user:
establish a second communication link with the second wearable device being worn on the body of the user at a second point in time, wherein the second wearable device is a same type as the first wearable device;
receive a third set of measurement data of the first type from a second sensor of the second wearable device indicative of the physiological measurements from the user, wherein the second sensor is located proximate the first location of the user and the third set of measurement data corresponds to the first location of the user; and
generate calibration information for the second wearable device based on the third set of measurement data and at least one of the first set of measurement data or the second set of measurement data corresponding to the first location of the user, wherein the calibration information is configured to:
align the third set of measurement data with the first set of measurement data or the second set of measurement data; and
calibrate the second wearable device based on the first set of measurements data taken by the first sensor at the first location of the user and the third set of measurement data taken by the second sensor at the first location of the user; and
a communication device coupled to the processing device, wherein the communication device is configured to:
in response to the second wearable device being worn on the body, send the calibration information to the second wearable device; and
in response to receiving the calibration information, the second wearable device is calibrated to generate the third set of measurement data, at the first location of the user, wherein the third set of measurement data is a continuation of the first set of measurement data.

12. The device of claim 11, further configured to establish a communication link between the first wearable device and the second wearable device.

13. The device of claim 11, further configured to establish a communication link to relay the calibration information from the first wearable device to the second wearable device.

14. The device of claim 11, further configured to normalize the first set of measurement data from the first wearable device with the third set of measurement of data from the second wearable device.

15. The device of claim 11, further configured to:
detect when the first wearable device is within a threshold distance of the device; and
establish a communication link with the first wearable device when the first wearable device is within the threshold distance.

16. The device of claim 11, further configured to provide wireless power to the first wearable device.

17. The device of claim 11, further configured to communicate firmware updates, software update, or operating system updates to the first wearable device in response to the second set of measurement data indicating the first wearable device is not engaged with the body and the first wearable device receiving power for charging.

18. The device of claim 11, further configured to:
receive selected medical information from another device; and
communicate the selected medical information to the first wearable device.

19. The device of claim 11, further configured to analyze the first set of measurement data, the second set of measurement data, or the third set of measurement data to determine a selected medical diagnosis.

20. A device, comprising:
a communication system configured to send and receive information between a first swappable wearable device and a second swappable wearable device; and
a processing device coupled to the communication system, the processing device being configured to:
establish a first communication link with the first swappable wearable device being worn at a location on a body of a user at a first point in time;
receive a first set of measurement data of a first type from a first sensor of the first wearable device indicative of physiological measurements from the user;
receive a second set of measurement data from the first sensor;
determine that the second set of measurement data indicates that the first swappable wearable device is not engaged with the body;

in response to the first swappable wearable device being removed from the body and replaced with a second swappable wearable device at the location on the body of the user:
   establish a second communication link with the second swappable wearable device being worn on the body of the user at a second point in time;
   receive a third set of measurement data from second sensor of the second swappable wearable device indicative of the physiological measurements from the user; and
   generate calibration information for the second swappable wearable device based on the third set of measurement data and at least one of the first set of measurement data or the second set of measurement data corresponding to the location, wherein the calibration information is configured to:
      align the third set of measurement data with the first set of measurement data or the second set of measurement data; and
      calibrate the second swappable wearable device based on the first set of measurements data taken by the first sensor at the location and the third set of measurement data taken by the second sensor at the location; and
   communicate the calibration information to the second swappable wearable device, and in response to receiving the calibration information, the second swappable wearable device is calibrated to generate the third set of measurement data at the location, wherein the third set of measurement data is a continuation of the first set of measurement data.

21. The device of claim 19, wherein the device is a wearable device or a non-wearable device.

* * * * *